United States Patent [19]

Marschner et al.

[11] Patent Number: 5,241,055
[45] Date of Patent: Aug. 31, 1993

[54] REACTIVE DYES WITH A REACTIVE SYSTEM BASED ON ALKENYLSULFONYL AND BENZYL COMPOUNDS AS INTERMEDIATES THEREFOR

[75] Inventors: Claus Marschner; Joerg L. Jessen, both of Speyer; Klaus Pandl, Ludwigshafen; Manfred Patsch, Wachenheim, all of Fed. Rep. of Germany

[73] Assignee: BASF Aktiengesellschaft, Ludwigshafen, Fed. Rep. of Germany

[21] Appl. No.: 899,943

[22] Filed: Jun. 17, 1992

Related U.S. Application Data

[63] Continuation of Ser. No. 618,814, Nov. 27, 1990, abandoned.

[30] Foreign Application Priority Data

Dec. 19, 1989 [DE] Fed. Rep. of Germany ....... 3941810

[51] Int. Cl.$^5$ ............................................. C09B 47/28
[52] U.S. Cl. .................................... 534/618; 534/642; 540/126; 540/131; 544/76; 544/206; 544/207; 552/227
[58] Field of Search ................ 534/642, 618; 540/126, 540/131; 544/76, 206, 207; 552/227

[56] References Cited

U.S. PATENT DOCUMENTS

| | | | |
|---|---|---|---|
| 3,553,189 | 1/1971 | Sugiyama et al. | 534/642 |
| 4,137,887 | 1/1979 | Fuchs et al. | 534/642 |
| 4,294,580 | 10/1981 | Henk et al. | 8/549 |
| 4,560,388 | 12/1985 | Rohrer | 534/642 X |
| 4,659,807 | 4/1987 | Segal | 534/642 |
| 4,663,440 | 5/1987 | Omura et al. | 534/642 |
| 4,686,286 | 8/1987 | Niwa et al. | 534/642 |
| 4,824,942 | 4/1989 | Yokoyawa et al. | 534/642 |
| 4,910,298 | 3/1990 | Yokogawa et al. | 534/642 |
| 4,960,872 | 10/1990 | Schlafer et al. | 534/642 |
| 4,975,539 | 12/1990 | Schlafer et al. | 534/642 |
| 5,037,965 | 8/1991 | Morimitsu et al. | 534/642 X |
| 5,070,189 | 12/1991 | Schlafer et al. | 534/642 |
| 5,166,338 | 11/1992 | Büch et al. | 544/76 |

FOREIGN PATENT DOCUMENTS

| | | |
|---|---|---|
| 10013765 | 8/1980 | European Pat. Off. |
| 0141359 | 6/1985 | European Pat. Off. |
| 10307817 | 3/1989 | European Pat. Off. |
| 0311969 | 4/1989 | European Pat. Off. |
| 0315046 | 5/1989 | European Pat. Off. |
| 0352682 | 1/1990 | European Pat. Off. |
| 2202820 | 7/1973 | Fed. Rep. of Germany |
| 2260827 | 7/1974 | Fed. Rep. of Germany |
| 2308663 | 8/1974 | Fed. Rep. of Germany |
| 3119349 | 12/1982 | Fed. Rep. of Germany |

OTHER PUBLICATIONS

The Chemistry of Synthetic Dyes, vol. III, 1970, pp. 303–304, R. Price, "The Chemistry of Metal Complex Dyestuffs".

Primary Examiner—Richard L. Raymond
Attorney, Agent, or Firm—Oblon, Spivak, McClelland, Maier & Neustadt

[57] ABSTRACT

Reactive dyes useful for dyeing or printing hydroxyl- or nitrogen-containing substrates have the formula

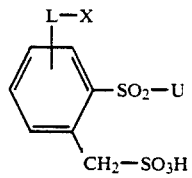

where
U is vinyl, propenyl or the radical of the formula

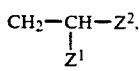

in which $Z^1$ is hydrogen or methyl and $Z^2$ is a group which is detachable under alkaline reaction conditions,
X is
a) the radical of a chromophore or
b) the radical of a coupling component to which (Abstract continued on next page.)

may be additionally attached the radical of a diazo component via an azo linkage and which may contain an additional reactive group, and L is a) a bridge member of the formula

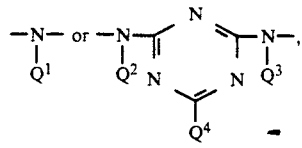

where $Q^1$ is hydrogen or $C_1$–$C_4$-alkyl, $Q^2$ and $Q^3$ are each independently of the other hydrogen or $C_1$–$C_4$-alkyl, and $Q^4$ is a leaving group, or b) an azo linkage, the radical X-L being bonded to the benzene ring meta or para to the $CH_2$-$SO_3H$ group, and their preparation may involve novel benzyl compounds as intermediates.

5 Claims, No Drawings

REACTIVE DYES WITH A REACTIVE SYSTEM BASED ON ALKENYLSULFONYL AND BENZYL COMPOUNDS AS INTERMEDIATES THEREFOR

This application is a continuation of application Ser. No. 07/618,814, filed on Nov. 27, 1990, now abandoned.

The present invention relates to reactive dyes of the formula I

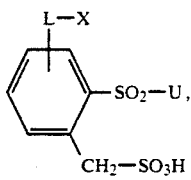

where
U is vinyl, propenyl or the radical of the formula

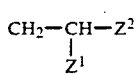

in which $Z^1$ is hydrogen or methyl and $Z^2$ is a group which is detachable under alkaline reaction conditions, X is
a) the radical of a chromophore which may contain a further reactive group and is derived from a metallized or unmetallized monoazo or disazo dye, from a triphendioxazine, from an anthraquinone, from a copper formazan or from a metallized phthalocyanine, or
b) the radical of a coupling component to which may be additionally attached the radical of a diazo component via an azo linkage and which may contain an additional reactive group, and L is
a) a bridge member of the formula

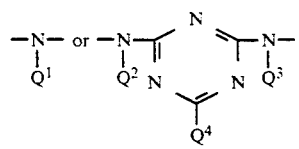

where $Q^1$ is hydrogen or $C_1$-$C_4$-alkyl, $Q^2$ and $Q^3$ are identical or different and each is independently of the other hydrogen or $C_1$-$C_4$-alkyl, and $Q^4$ is a leaving group, or
b) an azo linkage, the radical X-L being bonded to the benzene ring meta or para to the $CH_2$-$SO_3H$ group, and to a process for dyeing or printing hydroxyl- or nitrogen-containing substrates using the novel dyes.

The present invention also relates to novel benzyl compounds which are intermediates for these dyes.

EP-A-307 817 discloses double attachment reactive dyes which are derived from metallized or unmetallized azo dyes and exhibit a double reactive system based on a triazine/(sulfonylmethyl)aniline derivative.

Moreover, earlier patent application no. EP-A-352 682 describes double attachment reactive dyes based on various chromophores whose double reactive system is derived from a benzene derivative containing alkenylsulfonyl and alkenylsulfonylmethyl radicals.

It is an object of the present invention to provide novel reactive dyes having advantageous application properties. The new dyes should be suitable in particular for the cold pad-batch process and should be notable in particular for high yields of fixation and high fiber-dye bond stabilities. In addition, the unfixed portions on the fiber should be easy to wash off.

We have found that this object is achieved by the reactive dyes of the abovementioned formula I.

Any alkyl occurring in the abovementioned formula I is straight-chain or branched.

$Z^2$ in the formula I is a group which is detachable under alkaline reaction conditions. Such groups are for example chlorine, $OSO_3H$, $SSO_3H$, $OP(O)(OH)_2$, $C_1$-$C_4$-alkylsulfonyloxy, substituted or unsubstituted phenylsulfonyloxy, $C_1$-$C_4$-alkanoyloxy, $C_1$-$C_4$-dialkylamino,

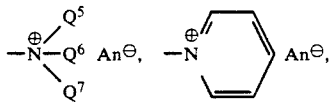

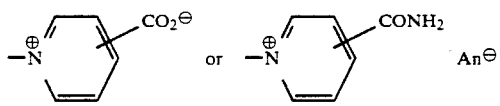

where $Q^5$, $Q^6$ and $Q^7$, are identical or different and each is independently of the others $C_1$-$C_4$-alkyl or benzyl and $An^\ominus$ is in each case an anion. Suitable anions $A^\ominus$ are for example fluoride, chloride, bromide, iodide, mono-, di- or trichloroacetate, methylsulfonate, phenylsulfonate and 2- or 4-methylphenylsulfonate.

$Q^4$ in the formula I is a leaving group. A leaving group is for example a radical of the formula

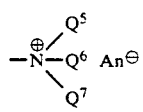

where $Q^5$, $Q^6$, $Q^7$, and $An^\ominus$ are each as defined above, but is preferably fluorine, chlorine or bromine.

$Q^1$, $Q^2$, $Q^3$, $Q^5$, $Q^6$ and $Q^7$ are each for example methyl, ethyl, propyl, isopropyl, butyl, isobutyl or sec-butyl.

The fiber-reactive radical of the formula II

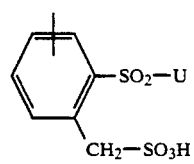

where U is as defined above, will hereinafter be referred to as "E".

Preference is given to reactive dyes of the formula Ia

 X-L-E¹     (Ia)

where X and L are each as defined above and $E^1$ is a radical of the formula IIa

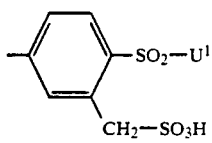

(IIa)

where
U¹ is vinyl or the radical of the formula -CH₂-CH₂-Z², where Z² is as defined above.

In addition to the reactive system E, the radical X may carry further fiber-reactive radicals. Such radicals are derived for example from triazine, pyrimidine or vinylsulfonyl compounds.

X in the formula I is for example the radical of a coupling component to which may in addition be attached via an azo linkage the radical of a diazo component and which may contain an additional reactive group. In this case the double reactive radical E is linked to the radical X via an azo linkage (—N=N—).

Dyes of this class conform to the formula IVa or IVb

(IVa)

(IVb)

where K is the radical of a coupling component, D is the radical of a diazo component, a is 1 or 2, and E is as defined above.

Useful dyes of this class are for example watersoluble azo dyes, in particular monoazo dyes of the formula IVa (a=1) or disazo dyes of the formula IVa (a=2) or IVb which possess hydroxysulfonyl and/or carboxyl groups.

Important coupling components HK are derived for example from compounds of the benzene, naphthalene, pyrazolone, pyridone or hydroxypyrimidine series.

Important diazo components D-NH₂ are derived for example from compounds of the aniline or aminonaphthalene series.

Particular preference is given to dyes of the formula V

(V)

where E¹ is as defined above and K¹ is the radical of a coupling component of the naphthalene, pyrazole, pyridone or hydroxypyrimidine series which may contain a further fiber-reactive group, in particular an E group.

Particular preference is further given to dyes of the formula VI

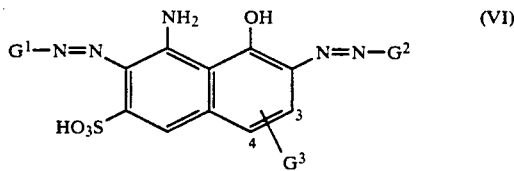

(VI)

where one of G¹ and G² is E¹, which is as defined above, and the other is D¹, which is a radical of a diazo component of the aniline or naphthalene series which may possess a further fiber-reactive group, in particular an E group, and G³ is hydroxysulfonyl in ring position 3 or 4.

X in the formula I may also be for example the metallized or unmetallized radical of an azo dye. Suitable azo dyes from which such radicals are derived are known per se and have been described in large numbers, for example in K. Venkataraman, The Chemistry of Synthetic Dyes, Vol. VI, Academic Press, New York, London, 1972. The azo dyes conform to the formula VII

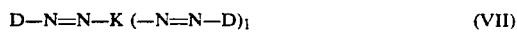

(VII)

where D is the radical of a diazo component, K is the radical of a coupling component, and l is 0 or 1.

Useful dyes from which the radical X is derived are for example water-soluble azo dyes, in particular monoazo dyes, of the formula VII (l=0) which may have hydroxysulfonyl and/or carboxyl groups.

Preferably, the radical X is derived from nonmetallized azo dyes, in particular from those which contain sulfo and/or carboxyl groups, of which those which have from 1 to 6 sulfo groups are particularly noteworthy.

Important azo dyes from which the radical X is derived are for example those of the phenyl-azo-naphthalene, phenyl-azo-1-phenylpyrazol-5-one, phenyl-azo-benzene, naphthyl-azo-benzene, phenyl-azo-aminonaphthalene, naphthyl-azo-naphthalene, napht-hyl-azo-1-phenylpyrazol-5-one, phenyl-azo-pyridone, phenyl-azo-aminopyridine, naphthylazo-pyridone, naphthyl-azo-aminopyridine or stilbyl-azobenzene series.

Particular preference is given to reactive dyes of the formula VIII

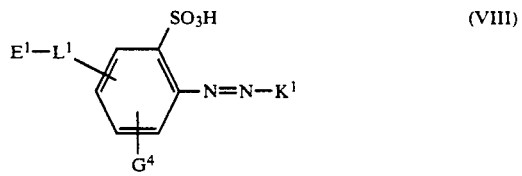

(VIII)

where E¹ is as defined above, L¹ is the radical of the formula

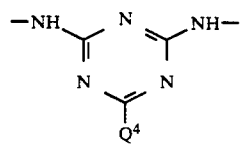

where Q⁴ is as defined above, G⁴ is hydrogen, C₁-C₄-alkyl, C₁-C₄-alkoxy, chlorine or hydroxysulfonyl, and K¹ is the radical of a coupling component of the naphthalene, pyrazolone, pyridone or hydroxypyrimidine series which may contain a further fiber-reactive group.

Particular preference is further given to reactive dyes of the formula IX

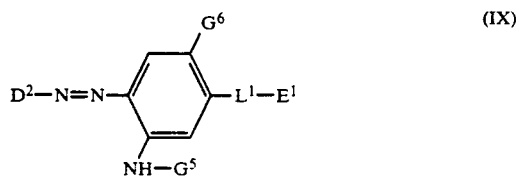

(IX)

where E¹ and L¹ are each as defined above, G⁵ is C₁-C₄-alkanoyl, carbamoyl, C₁-C₄-monoalkylcarbamoyl or -dialkylcarbamoyl, phenylcarbamoyl or cyclohexylcarbamoyl, G⁶ is hydrogen, C₁-C₄-alkyl, C₁-C₄-alkoxy, hydroxysulfonyl or chlorine, and $D^2$ is the radical of a diazo component of the aniline or naphthalene series devoid of any further fiber-reactive group.

Particular preference is further given to reactive dyes of the formula X

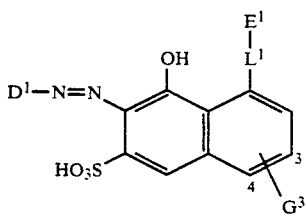

where $D^1$, $E^1$ and $L^1$ are each as defined above and $G^3$ is hydroxysulfonyl in ring position 3 or 4.

Particular preference is further given to reactive dyes of the formula XI

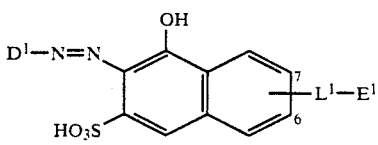

where $D^1$, $E^1$ and $L^1$ are each as defined above and the group —L—$E^1$ is in ring position 6 or 7.

Useful compounds also include those of the formula XII

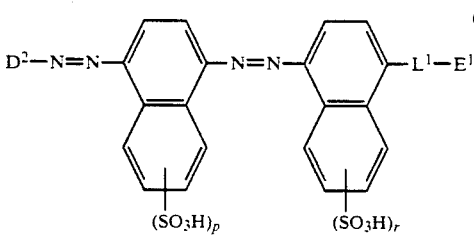

where $D^2$, $E^1$ and $L^1$ are each as defined above and p and r are each independently of the other 0, 1 or 2.

Useful compounds also include those of the formula XIII

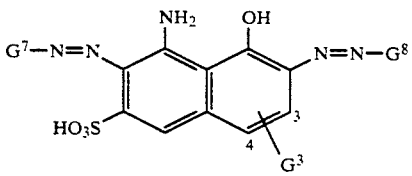

where $G^3$ is as defined above and one of $G^7$ and $G^8$ is $D^1$, which is as defined above, and the other is the radical

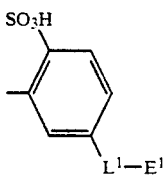

in which $L^1$ and $E^2$ are each as defined above.

Such aromatic radicals $D^1$ and $D^2$ of diazo components of the aniline or aminonaphthalene series which do not carry any fiber-reactive groups are derived for example from amines of the formulae XIV a-f

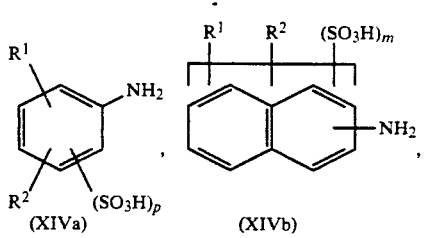

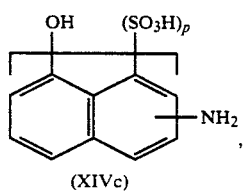

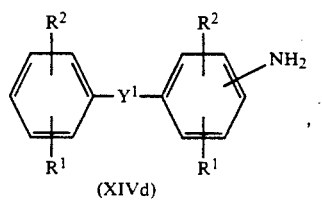

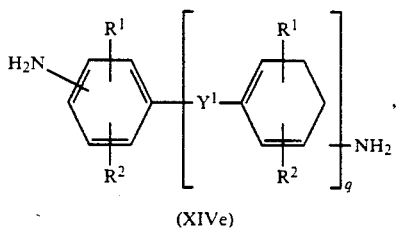

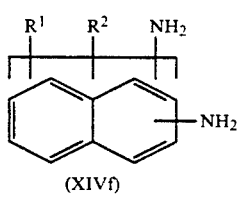

where
m is 0, 1, 2 or 3,
p is 0, 1 or 2,
q is 0 or 1,
$R^1$ is hydrogen, methyl, ethyl, methoxy, ethoxy, acetyl, cyano, carboxyl, hydroxysulfonyl, $C_1$-$C_4$-alkoxycarbonyl, hydroxyl, carbamoyl, $C_1$-$C_4$-monoalkylcarbamoyl or -dialkylcarbamoyl, fluorine, chlorine, bromine or trifluoromethyl,
$R^2$ is hydrogen, methyl, ethyl, methoxy, ethoxy, cyano, carboxyl, hydroxysulfonyl, acetylamino, $C_1$-$C_4$-alkoxycarbonyl, carbamoyl, $C_1$-$C_4$-monoalkylcarbamoyl or -dialkylcarbamoyl, fluorine, chlorine, nitro, sulfamoyl, $C_1$-$C_4$-monoalkylsulfamoyl, or -dialkylsulfamoyl, $C_1$-$C_4$-alkylsulfonyl, phenylsulfonyl or phenoxy, and
$Y^1$ is a direct bond, oxygen, sulfur or the group —NHCO—, —CONH—, —CO—, —NHSO$_2$—, —SO$_2$NH—, —SO$_2$—, —CH=CH—, —CH$_2$—CH$_2$—, —CH$_2$—, —NH—, or —N=N—.

Preference is given here to those components in which R¹ is hydrogen, methyl, methoxy, carboxyl, hydroxysulfonyl, hydroxyl or chlorine, R² is hydrogen, methyl, methoxy, carboxyl, hydroxysulfonyl, acetylamino or chlorine, and Y¹ is the group —CO—, —SO₂—, —CH=CH—, —CH₂—CH₂—, —CH₂— or —N=N—.

Aromatic amines which are suitable for use as diazo components and which conform to the formula XIVa, XIVb, XIVc or XIVd are for example aniline, 2-methoxyaniline, 2-methylaniline, 4-chloro-2-aminoanisole, 4-methylaniline, 4-methoxyaniline, 2-methoxy-5-methylaniline, 2,5-dimethoxyaniline, 2,5-dimethylaniline, 2,4-dimethylaniline, 2,5-diethoxyaniline, 2-chloroaniline, 3-chloroaniline, 4-chloroaniline, 2,5-dichloroaniline, 4-chloro-2-nitroaniline, 4-chloro-2-methylaniline, 3-chloro-2-methylaniline, 4-chloro-2-aminotoluene, 4-phenylsulfonylaniline, 2-ethoxy-1-naphthylamine, 1-naphthylamine, 2-naphthylamine, 4-methylsulfonylaniline, 2,4-dichloroaniline-5-carboxylic acid, 2-aminobenzoic acid, 4-aminobenzoic acid, 3-aminobenzoic acid, 3-chloroaniline-6-carboxylic acid, aniline-2- or -3- or -4-sulfonic acid, aniline-2,5-disulfonic acid, aniline-2,4-disulfonic acid, aniline-3,5-disulfonic acid, 2-aminotoluene-4-sulfonic acid, 2-aminoanisole-4-sulfonic acid,2-aminoanisole-5-sulfonic acid,2-ethoxyaniline-5-sulfonic acid,2-ethoxyaniline-4-sulfonic acid, 4-hydroxysulfonyl-2-aminobenzoic acid, 2,5-dimethoxyaniline-4-sulfonic acid, 2,4-dimethoxyaniline-5-sulfonic acid, 2-methoxy-5-methylaniline-4-sulfonic acid, 4-aminoanisole-3-sulfonicacid,4-aminotoluene-3-sulfonic acid, 2-aminotoluene-5-sulfonic acid, 2-chloroaniline-4-sulfonic acid, 2-chloroaniline-5-sulfonic acid, 2-bromoaniline-4-sulfonic acid, 2,6-dichloroaniline-4-sulfonic acid,2,6-dimethylaniline-3-or-4-sulfonicacid,3-acetylamino-6-sulfonic acid, 4-acetylamino-2-hydroxysulfonylaniline, 1-aminonaphthalene-4-sulfonic acid, 1-aminonaphthalene-3-sulfonic acid, 1-aminonaphthalene-5-sulfonic acid, 1-aminonaphthalene-6-sulfonic acid, 1-aminonaphthalene-7-sulfonic acid, 1-aminonaphthalene-3,7-disulfonic acid, 1-aminonaphthalene-3,6,8-trisulfonic acid, 1-aminonaphthalene-4,6,8-trisulfonic acid, 2-naphthylamine-5-sulfonic acid, or -6- or -8-sulfonic acid, 2-aminonaphthalene-3,6,8-trisulfonic acid, 2-aminonaphthalene-6,8-disulfonic acid, 2-aminonaphthalene-1,6-disulfonic acid, 2-aminonaphthalene-1-sulfonic acid, 2-amino-naphthalene-1,5-disulfonic acid, 2-aminonaphthalene-3,6-disulfonic acid, 2-aminonaphthalene-4,8-disulfonic acid, 2-aminophenol-4-sulfonic acid, 2-aminophenol-5-sulfonic acid, 3-aminophenol-6-sulfonic acid, 1-hydroxy-2-aminonaphthalene-5,8- or -4,6-disulfonic acid, 4-aminodiphenylamine,4-amino-4'-methoxydiphenylamine,4-amino-4'-methoxydiphenylamine-3-sulfonic acid, 4-(2'-methylphenylazo)-2-methylaniline, 4-aminoazobenzene, 4'-nitrophenylazo-1-aminonaphthalene, 4-(6'-hydroxysulfonylnaphthylazo)-1-aminonaphthalene, 4-(2',5'-dihydroxysulfonylphenylazo)-1-aminonaphthalene, 4'-amino-3'-methyl-3-nitrobenzophenone, 4-aminobenzophenone, 4-(4'-aminophenylazo)benzenesulfonic acid, 4-(4'-amino-3'-methoxyphenylazo)benzenesulfonic acid and 2-ethoxy-1-naphthylamine-6-sulfonic acid.

Aromatic diamines which are suitable for use as tetrazo components and which conform to the formula XIVe or XIVf are for example 1,3-diaminobenzene, 1,3-diaminobenzene-4-sulfonic acid, 1,4-diaminobenzene, 1,4-diaminobenzene-2-sulfonic acid, 1,4-diamino-2-methylbenzene, 1,4-diamino-2-methoxybenzene, 1,3-diamino-4-methylbenzene, 1,3-diaminobenzene-5-sulfonic acid, 1,3-diamino-5-methylbenzene, 1,6-diaminonaphthalene-4-sulfonic acid, 2,6-diaminonaphthalene-4,8-disulfonicacid,3,3'-diaminodiphenyl sulfone, 4,4'-diaminodiphenyl sulfone, 4,4'-diaminostilbene-2,2'-disulfonic acid, 2,7'-diaminodiphenylsulfone, 2,7'-diaminodiphenylsulfone-4,5-disulfonic acid, 4,4'-diaminobenzophenone, 4,4'-diamino-3,3'-dinitrobenzophenone, 3,3'-diamino-4,4'-dichlorobenzophenone, 4,4'- or 3,3'-diaminobiphenyl, 4,4'-diamino-3,3'-dichlorobiphenyl, 4,4'-diamino-3,3'-dimethoxy- or -3,3'-dimethyl- or -2,2'-dimethyl- or -2,2'-dichloro- or -3,3'-diethoxybiphenyl, 4,4'-diamino-3,3'-dimethyl-6,6'-dinitrobiphenyl, 4,4'-diaminobiphenyl-2,2'- or -3,3'-disulfonic acid, 4,4'-diamino-3,3'-dimethyl- or -3,3'-dimethoxy or -2,2'-dimethoxybiphenyl-6,6'-disulfonic acid, 4,4'-diamino-2,2', 5,5'-tetrachlorobiphenyl, 4,4'-diamino-3,3'-dinitrobiphenyl, 4,4'-diamino-2,2'-dichloro-5,5'-dimethoxybiphenyl, 4,4'-diaminobiphenyl-2,2'- or -3,3'-dicarboxylic acid, 4,4'-diamino-3,3'-dimethylbiphenyl-5,5'-disulfonic acid, 4,4'-diamino-2-nitrobiphenyl, 4,4'-diamino-3-ethoxy- or -3-hydroxysulfonylbiphenyl, 4,4'-diamino-3,3'-dimethylbiphenyl-5-sulfonic acid, 4,4'-diaminodiphenylmethane, 4,4'-diamino-3,3'-dimethyldiphenylmethane, 4,4'-diamino-2,2', 3,3'-tetramethyldiphenylmethane, 4,4'-diaminodiphenylethane, 4,4'-diaminostilbene or 4,4'-diaminodiphenylmethane-3,3'-dicarboxylic acid.

Those aromatic radicals D¹ of diazo components of the aniline or aminonaphthalene series which can carry a fiber-reactive radical E are derived for example from amines of the formulae XVa-c

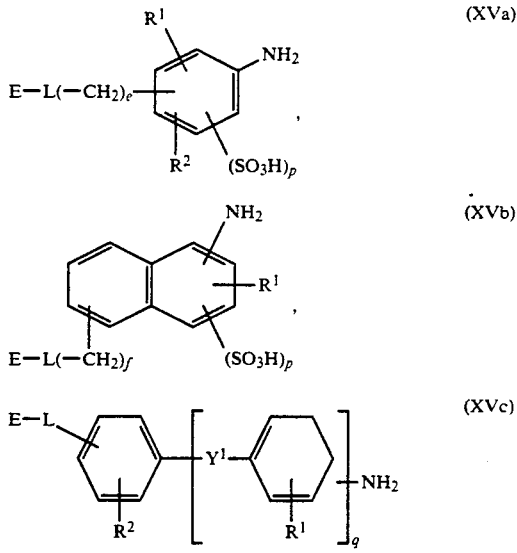

where L, R¹, R², p, q, Y¹ and E are each as defined above and e and f are identical or different and each is independently of the other 0 or 1.

Aromatic amines which form the basis of the derivatives of the formula XVa, XVb or XVc with the fiber-reactive radical E are for example 1,3-diaminobenzene, 1,3-diaminobenzene-4-sulfonic acid, 1,3-diaminobenzene-4,6-disulfonic acid, 1,4-diaminobenzene, 1,4-diaminobenzene-2-sulfonic acid, 1,4-diaminobenzene-2,5-disulfonic acid, 1,4-diamino-2-methylbenzene, 1,4-diamino-2-methoxybenzene,1,3-diamino-4-methylbenzene,1,4-diaminobenzene-2,6-disulfonic acid, 1,5- diamino-4-methylbenzene-2-sulfonic acid, 1,5-diamino-4-methoxybenzene-2-sulfonic acid, 1,6-diaminonaphth-2-ol-4-sulfonic acid, 1,6-diaminonaphthalene-4-sulfonic acid, 2,6-diaminonaphthalene-4,8-disulfonic acid, 2,6-diaminonaphth-1-ol-4,8-disulfonic acid, 1,3-diaminobenzene-5-sulfonic acid, 1,3-diamino-5-methylbenzene, 2,6-diaminophenol-4-sulfonic acid, 5-(aminomethyl)-2-aminonaphthalene-1-sulfonic acid, 5-(N-methylaminomethyl)-2-aminonaphthalene-1-sulfonic acid, 4,4'-diaminostilbene-3,3'-dicarboxylic acid, 4-(N-methylaminomethyl)aniline-2-sulfonic acid or 3-(N-methylaminomethyl)aniline-6-sulfonic acid.

The radicals K of the coupling component are preferably derived from the aniline, naphthalene, pyrazole, pyridine, pyrimidine, indole or acylacetarylide series and may also carry fiber-reactive groups.

Aniline- and naphthalene-based coupling components which are devoid of fiber-reactive groups correspond for example to the compounds of the formulae XVIa-g

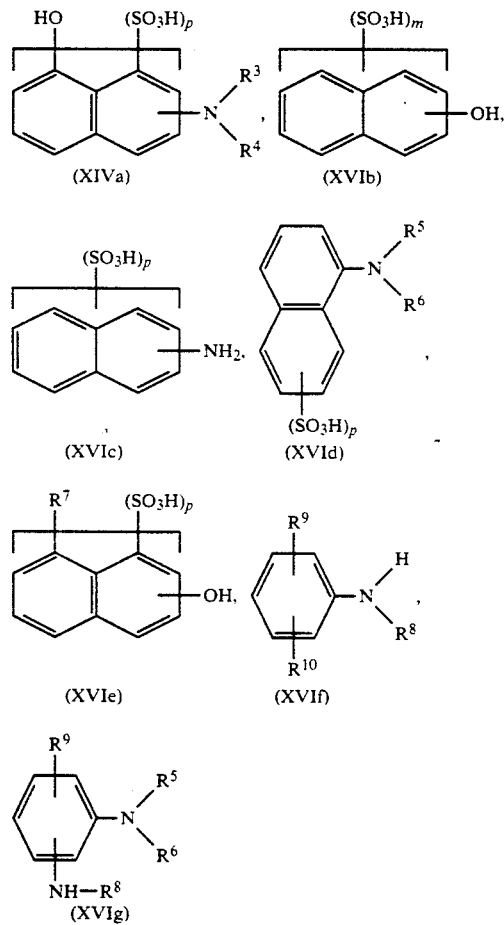

where
R$^3$ is hydrogen or C$_1$-C$_4$-alkyl,
R$^4$ is hydrogen, C$_1$-C$_4$-alkyl or phenyl which may be monosubstituted or disubstituted by C$_1$-C$_4$-alkyl, C$_1$-C$_4$-alkoxy, chlorine, bromine or hydroxysulfonyl,
R$^5$ is hydrogen or C$_1$-C$_4$-alkyl which may be substituted by hydroxyl, cyano, carboxyl, hydroxysulfonyl, hydroxysulfonyloxy, methoxycarbonyl, ethoxycarbonyl or acetoxy,
R$^6$ is hydrogen, C$_1$-C$_4$-alkyl, which may be hydroxyl-, cyano-, carboxyl-, hydroxysulfonyl-, hydroxysulfonyloxy-, methoxycarbonyl-, ethoxycarbonyl- or acetoxy-substituted, benzyl or phenyl which may be substituted by C$_1$-C$_4$-alkyl, C$_1$-C$_4$-alkoxy, chlorine or hydroxysulfonyl,
R$^7$ is C$_1$-C$_6$-alkylureido, phenylureido, which may be chlorine-, methyl-, methoxy-, nitro-, hydroxysulfonyl- or carboxyl-substituted, C$_1$-C$_6$-alkanoylamino, cyclohexanoylamino, benzoylamino, which may be chlorine-, methyl-, methoxy-, nitro-, hydroxysulfonyl- or carboxyl-substituted, or hydroxyl,
R$^8$ is hydrogen, C$_1$-C$_6$-alkyl, in particular C$_1$-C$_4$-alkyl, which may in either case be phenyl-, C$_1$-C$_4$-alkoxy-, hydroxyl-, phenoxy- or C$_1$-C$_4$-alkanoyloxy-substituted, C$_5$-C$_7$-cycloalkyl, hydroxysulfonylphenyl, C$_1$-C$_4$-alkanoyl, carbamoyl, C$_1$-C$_4$-monoalkylcarbamoyl or -di-alkylcarbamoyl, phenylcarbamoyl or cyclohexylcarbamoyl,
R$^9$ is methoxy, ethoxy, chlorine, bromine, acetylamino, amino, ureido, methylsulfonylamino, ethylsulfonylamino, dimethylaminosulfonylamino, methylamino, ethylamino, dimethylamino or diethylamino,
R$^{10}$ is hydrogen, methyl, ethyl, methoxy, ethoxy, chlorine or bromine, and
p and m are each as defined above.

Specific examples are o- or m-toluidine, o- or m-anisidine, cresidine, 2,5-dimethylaniline, 2,5-dimethoxyaniline, m-aminoacetanilide, 3-amino-4-methoxyacetanilide, 3-amino-4-methylacetanilide, m-aminophenylurea, N-methylaniline, N-methyl-m-toluidine, N-ethylaniline, N-ethyl-m-toluidine, N-(2-hydroxyethyl)aniline and N-(2-hydroxyethyl)-m-toluidine.

Naphtholsulfonic acids are for example 1-naphthol-3-sulfonic acid, 1-naphthol-4-sulfonic acid, 1-naphthol-5-sulfonic acid, 1-naphthol-8-sulfonic acid, 1-naphthol-3,6-disulfonic acid, 1-naphthol-3,8-disulfonic acid, 2-naphthol-5-sulfonic acid, 2-naphthol-6-sulfonic acid, 2-naphthol-7-sulfonic acid, 2-naphthol-8-sulfonic acid, 2-naphthol-3,6-disulfonicacid,2-naphthol-6,8-disulfonic acid, 2-naphthol-3,6,8-trisulfonic acid, 1,8-dihydroxynaphthalene-3,6-disulfonic acid, 2,6-dihydroxynaphthalene-8-sulfonic acid or 2,8-dihydroxynaphthalene-6-sulfonic acid.

Further examples are 1-naphthylamine, N-phenyl-1-naphthylamine, N-ethyl-1-naphthylamine, N-phenyl-2-naphthylamine, 1-naphthol, 2-naphthol, 1,5-dihydroxynaphthalene, 1,6-dihydroxynaphthalene, 1,7-dihydroxynaphthalene and 2,7-dihydroxynaphthalene.

Aminonaphthalenesulfonic acids are for example 1-naphthylamine-6-sulfonic acid, 1-naphthylamine-7-sulfonic acid, 1-naphthylamine-8-sulfonic acid, 2-naphthylamine-3,6-disulfonic acid, 2-naphthylamine-5,7-disulfonic acid and 2-naphthylamine-6,8-disulfonic acid.

Aminonaphtholsulfonic acids are for example 1-amino-5-hydroxynaphthalene-7-sulfonic acid, 1-amino-8-hydroxynaphthalene-4-sulfonic acid, 1-amino-8-hydroxynaphthalene-2,4-disulfonic acid, 1-amino-8-hydroxynaphthalene-3,6-disulfonic acid, 1-amino-8-hydroxynaphthalene-4,6-disulfonic acid, 2-amino-5-hydroxynaphthalene7-sulfonic acid, 2-amino-8-hydroxynaphthalene-6-sulfonic acid, 2-amino-8-hydroxynaphthalene-3,6-disulfonic acid, 2-amino-5-hydroxynaphthalene-1,7-disulfonic acid, 1-acetylamino-8-hydroxynaphthalene-3,6-disulfonic acid, 1-benzoylamino-8-hydroxynaphthalene-3,6-disulfonic acid,1-acetylamino-8- hydroxynaphthalene-4,6-disulfonic acid, 1-benzoylamino-8-hydroxynaphthalene-4,6-disulfonic acid, 1-acetylamino-5-hydroxynaphthalene-7-sulfonic acid, 2-methylamino-8-hydroxynaphthalene-6-sulfonic acid, 2-methylamino-8-hydroxynaphthalene-6-sulfonic acid, and 2-(3'- or 4'-hydroxysulfonylphenyl)amino-8-hydroxynaphthalene-6-sulfonic acid.

Of particular importance are coupling components which contain sulfo and/or carboxyl groups and which couple ortho or para to a hydroxyl and/or amino group.

Examples of such coupling components are 2-acetylamino-5-hydroxynaphthalene-7-sulfonic acid, 2-acetylamino-8-hydroxynaphthalene-6-sulfonic acid, 1-acetylamino-8-hydroxynaphthalene-3,6-disulfonic acid, 1-benzoylamino-8-hydroxynaphthalene-3,6-disulfonic acid, 1-acetylamino-8-hydroxynaphthalene-4,6-disulfonic acid and 1-benzoylamino-8-hydroxynaphthalene-4,6-disulfonic acid.

Coupling components of the other series are for example pyrazolones, aminopyrazoles, 2,6-diaminopyridines, pyridones, hydroxypyrimidines, aminopyrimidines, indoles and acetoacetarylides.

Coupling components of this series which are free of fiber-reactive groups conform for example to the formulae XVIIa-f:

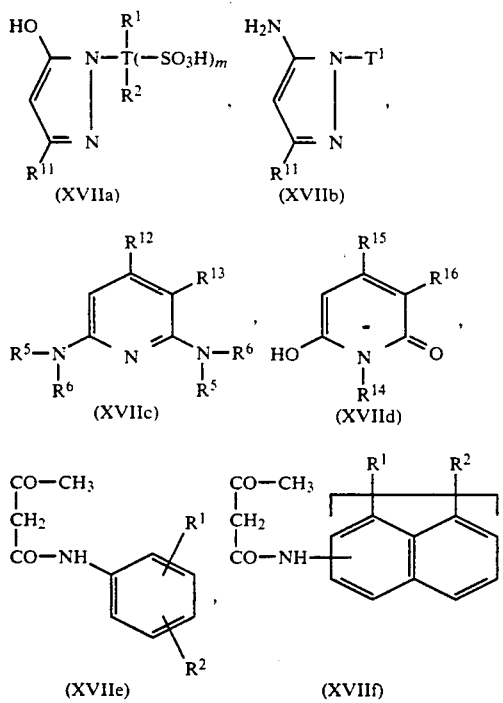

where
T is a benzene or naphthalene nucleus,
$T^1$ is $C_1-C_4$-alkyl, cyclohexyl, benzyl or phenyl which is monosubstituted or polysubstituted by fluorine, chlorine, bromine, methyl, methoxy, nitro, hydroxysulfonyl, carboxyl, acetyl, acetylamino, methylsulfonyl, sulfamoyl or carbamoyl,
$R^{11}$ is methyl, carboxyl, $C_1-C_4$-alkoxycarbonyl or phenyl,
$R^{12}$ is hydrogen or $C_1-C_4$-alkyl which may be substituted by methoxy, ethoxy or cyano,
$R^{13}$ is hydrogen, methyl, hydroxysulfonylmethyl, hydroxysulfonyl, cyano or carbamoyl, $R^{14}$ is hydrogen, $C_1-C_4$-alkyl, which may be phenyl-, hydroxysulfonylphenyl-, hydroxyl-, amino-, methoxy-, ethoxy-, carboxyl-, hydroxysulfonyl-, acetylamino-, benzoylamino- or cyano-substituted, cyclohexyl, phenyl which may be carboxyl-, hydroxysulfonyl-, benzoylamino-, acetylamino-, methyl-, methoxy-, cyano- or chlorine-substituted, or amino which is substituted by phenyl, $C_1-C_4$-alkyl, acetyl or benzoyl,
$R^{15}$ is $C_1-C_4$-alkyl, phenyl, hydroxyl, cyano, acetyl, benzoyl, carboxyl, methoxycarbonyl, carbamoyl or hydroxysulfonylmethyl, and
$R^{16}$ is hydrogen, chlorine, bromine, acetylamino, amino, nitro, hydroxysulfonyl, sulfamoyl, methylsulfonyl, phenylsulfonyl, carboxyl, methoxycarbonyl, acetyl, benzoyl, carbamoyl, cyano or hydroxysulfonylmethyl, and $R^1$, $R^2$, $R^5$, $R^6$ and m are each as defined above.

Suitable pyrazolone coupling components are for example 3-methyl-, 3-carboxy- or 3-($C_1-C_4$-alkoxycarbonyl)pyrazol-5-ones which may carry in the 1-position hydrogen, unsubstituted or methyl-, ethyl-, fluorine-, chlorine-, bromine-, trifluoromethyl-, methoxy-, ethoxy-, cyano-, phenoxy-, phenylsulfonyl-, methylsulfonyl-, hydroxysulfonyl-, acetylamino-, nitro-, hydroxyl-, carboxyl-, carbamoyl- or sulfamoyl-substituted phenyl or hydroxysulfonyl-substituted 1- or 2-naphthyl. Examples are 1-phenyl-, 1-(2'-chlorophenyl)-, 1-(2'-methoxyphenyl)-, 1-(2'-methylphenyl)-, 1-(1',5'-dichlorophenyl)-, 1-(2',6'-dichlorophenyl)-, 1-(2'-methyl-6'-chlorophenyl)-, 1-(2'-methoxy-5'-methylphenyl)-, 1-(2'-methoxy-5'-hydroxysulfonylphenyl)-, 1-(2',5'-dichloro-4'-hydroxysulfonylphenyl)-, 1-(2',5'-dihydroxysulfonylphenyl)-, 1-(2'-carboxyphenyl)-, 1-(3'-hydroxysulfonylphenyl)- 1-(4'-hydroxysulfonylphenyl)- or 1-(3'-sulfamoylphenyl)-3-carboxyl-pyrazol-5-one, 1-(3'- or 4'-hydroxysulfonylphenyl)-, 1-(2'-chloro-4'- or -5'-hydroxysulfonylphenyl)-, 1-(2'-methyl-4'-hydroxysulfonylphenyl)-, 1-(2',5'-dichlorophenyl)-, 1-(4',8'-dihydroxysulfonyl-1-naphthyl)-, 1-(6'-hydroxysulfonyl-1-naphthyl)-3-methylpyrazol-5-one, ethyl 1-phenylpyrazol-5-one-3-carboxylate, ethyl pyrazol-5-one-3-carboxylate and pyrazol-5-one-3-carboxylic acid.

Other coupling components of the pyrazole series are for example 1-methyl-, 1-ethyl-, 1-propyl-, 1-butyl-, 1-cyclohexyl-, 1-benzyl- or 1-phenyl-5-aminopyrazole, 1-(4'-chlorophenyl)- or 1-(4'-methylphenyl)-5-aminopyrazole and 1-phenyl-3-methyl-5-aminopyrazole.

Acetoacetanilides are in particular acetoacetanilide itself and derivatives thereof which are monosubstituted or polysubstituted in the phenyl nucleus by chlorine, methyl, ethyl, methoxy, ethoxy, acetylamino, hydroxysulfonyl, carboxyl, carbamoyl or sulfamoyl.

Coupling components derived from pyridine are for example the derivatives described in DE-A-2 260 827.

Suitable pyrimidine coupling components are for example the compounds listed in DE-A-2 202 820, DE-A-2 308 663 and DE-A-3 119 349. It is also possible to use barbituric acid and its N-substitution products. Suitable N-substituents here are in particular $C_1-C_4$-alkyl and substituted or unsubstituted phenyl.

Suitable indole coupling components are for example 2-methylindole, 2-phenylindole, 2-phenylindole5-sulfonic acid, 1-methyl-2-phenylindole, 1-(2'-hydroxyethyl)-, 1-(2'-carboxyethyl)- or 1-(2'-carbamoylethyl)-2-methylindole or -2-phenylindole.

Suitable pyridone coupling components are for example 1-ethyl-2-hydroxy-4-methyl-5-carbamoylpyrid-6-one, 1-(2'-hydroxyethyl)-2-hydroxy-4-methyl-5-carbamoylpyrid-6-one, 1-phenyl-2-hydroxy-4-methyl-5-carbamoylpyrid-6-one, 1-ethyl-2-hydroxy-4-methyl-5-cyanopyrid-6-one, 1-ethyl-2-hydroxy-4-methyl-5-hydroxysulfonylmethylpyrid-6-one, 1-methyl-2-hydroxy-4-methyl-5-cyanopyrid-6-one, 1-methyl-2-hydroxy-5-acetylpyrid-6-one, 1,4-dimethyl-2-hydroxy-5-cyanopyrid-6-one, 1,4-dimethyl-5-carbamoylpyrid-6-one, 2,6-dihydroxy-4-ethyl-5-cyanopyridine, 2,6-dihydroxy-4-ethyl-5-carbamoylpyridine, 1-ethyl-2-hydroxy-4-methyl-5-hydroxysulfonylmethylpyrid-6-one, 1-methyl-2-hydroxy-4-methyl-5-methylsulfonylpyrid-6-one and 1-carboxymethyl-2-hydroxy-4-ethyl-5-phenylsulfonylpyrid-6-one.

Coupling components K of the aniline or naphthalene series which contain fiber-reactive groups are for example compounds of the formulae XVIIIa-e:

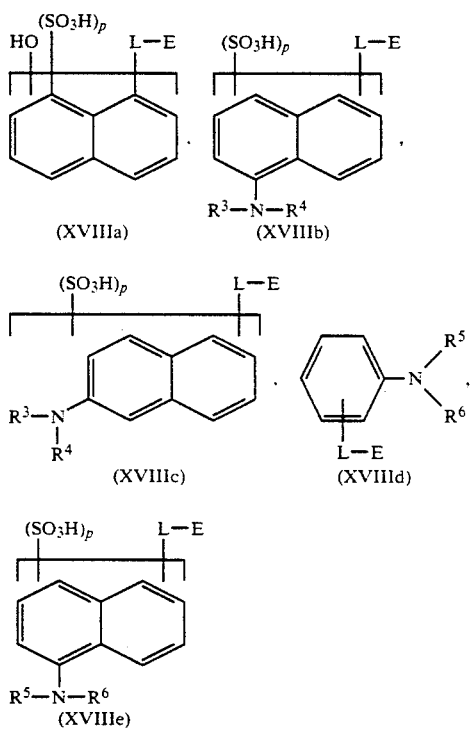

where L, $R^3$, $R^4$, $R^5$, $R^6$, E and p are each as defined above.

Coupling components of the pyrazolone, aminopyrazole, 2,6-diaminopyridine, pyridone, hydroxypyrimidine or aminopyrimidine, indole or acetoacetarylide series which contain fiber-reactive groups conform for example to the formulae XIXa-f:

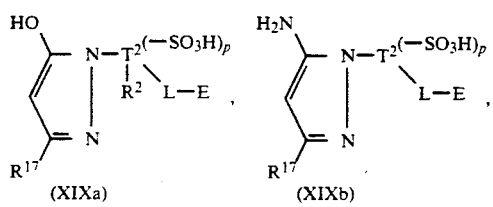

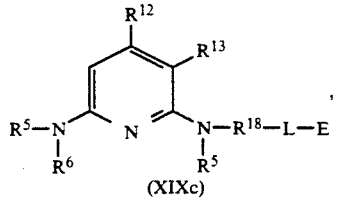

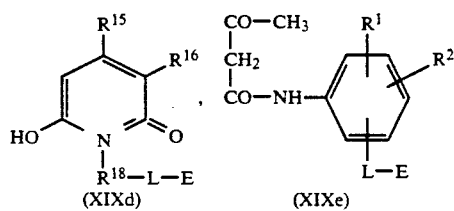

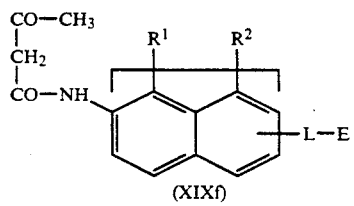

where $T^2$ is a benzene or naphthalene nucleus, $R^{17}$ is methyl, carboxyl, $C_1$–$C_4$-alkoxycarbonyl or phenyl, $R^{18}$ is $C_1$–$C_4$-alkyl, benzyl, phenylethyl or phenyl, which phenyl nuclei may each be additionally substituted by fluorine, chlorine, bromine, methyl, methoxy, cyano, hydroxysulfonyl, carboxyl, acetyl, nitro, carbamoyl or sulfamoyl, and L, $R^1$, $R^2$, $R^5$, $R^6$, $R^{12}$, $R^{13}$, $R^{15}$, $R^{16}$, p and E are each as defined above.

Pyrazolone coupling components which carry fiber-reactive radicals E are derived for example from the following pyrazolones: 1-(3'- or 4'-aminophenyl)-, 1-(2'-hydroxysulfonyl-5'-aminophenyl)- or 1-(2'-methoxy-5'-aminophenyl)-3-carboxypyrazol-5-one or 1-(3'- or 4'-aminophenyl)- or 1-(6'-amino-4',8'-dihydroxysulfonyl-naphth-2'-yl)-3-carboxypyrazol-5-one.

Instead of the azo dye residues the dyes of the formula I may also contain corresponding metal complex dye residues. Suitable complexing metals here are in particular copper, cobalt, chromium, nickel and iron, of which copper, cobalt and chromium are preferred.

These metallized groups are each preferably ortho to the azo group, for example in the form of o,o'-dihydroxy-, o-hydroxy-o'-carboxy-, o-carboxy-o'-amino- or o-hydroxy-o'-amino-azo groups.

X in the formula I may also be for example the residue of a copper formazan dye. Copper formazans are known per se and described for example in K. Venkataraman, The Chemistry of Synthetic Dyes, Vol. III, Academic Press, New York, London, 1970.

Particular preference is given to copper formazan dyes of the formula XX

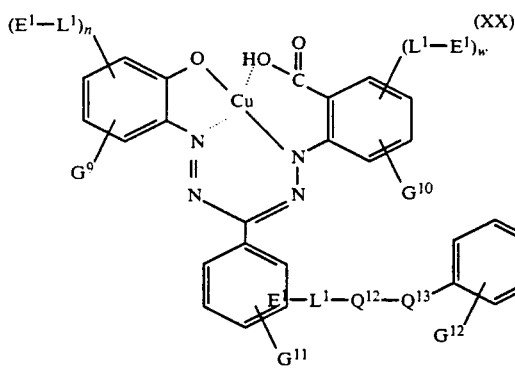

(XX)

where
- $G^9$, $G^{10}$ and $G^{11}$ are identical or different and each is independently of the others hydrogen or hydroxysulfonyl,
- n is 0 or 1,
- w is 0 or 1, and
- $E^1$ and $L^1$ are each as defined above, with the proviso that n and w are not 0 at one and the same time.

A method for preparing the formazans on which these dyes are based is described for example in EP-A-315 046.

X in the formula I may also be for example the residue of an anthraquinone dye. Anthraquinones are known per se and described for example in K. Venkataraman, The Chemistry of Synthetic Dyes, Vol. II, Academic Press, New York, 1952.

Particular preference is given to anthraquinone dyes of the formula XXI

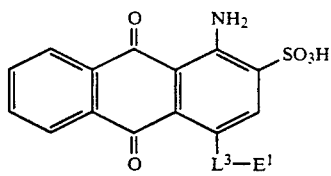

(XXI)

where
$L^3$ is imino or the radical

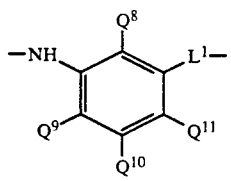

where $L^1$ is as defined above, $Q^8$ and $Q^9$ are identical or different and each is independently of the other hydrogen or methyl, and one of $Q^{10}$ and $Q^{11}$ is hydrogen or methyl and the other is hydroxysulfonyl, and $E^1$ is as defined above.

X in the formula I may also be for example the radical of a triphendioxazine dye. Triphendioxazines are known per se and described for example in EP-A-141 359 or EP-A-311 969.

Particular preference is given to triphendioxazine dyes of the formula XXII

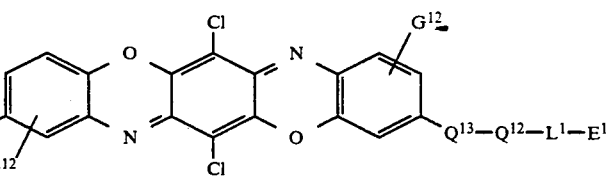

(XXII)

where
- $E^1$ and $L^1$ are each as defined above,
- $G^{12}$ is hydroxysulfonyl or the radical $SO_2$-$C_2H_4$-$OSO_3H$,
- $Q^{13}$ is oxygen, imino or $C_1$-$C_4$-alkylimino, and
- $Q^{12}$ is straight-chain or branched $C_2$-$C_4$-alkylene or phenylene.

X in the formula I may also be for example a residue of a metallized phthalocyanine dye. Phthalocyanines are known per se and described for example in F. H. Moser, D. L. Thomas, The Phthalocyanines, Vol. II, CRC Press, Boca Raton, Fla., 1983.

Particular preference is given to phthalocyanine dyes of the formula XXIII

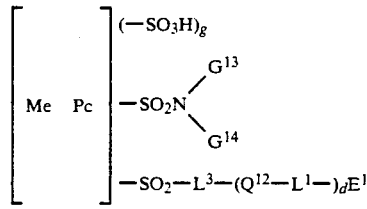

(XXIII)

where
- Pc is a phthalocyanine radical
- $G^{13}$ and $G^{14}$ are identical or different and each is independently of the other hydrogen or $C_1$-$C_4$-alkyl,
- $L^3$ is imino or $C_1$-$C_4$-alkylimino,
- d is 0, 1, 2 or 3,
- Me is copper or nickel,
- g is 0 or 1, and
- $L^1$, E and $Q^{12}$ are each as defined above.

The present invention further provides novel benzyl compounds of the formula III

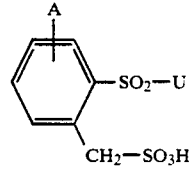

(III)

where
A is nitro or amino and
$U^1$ is vinyl, propenyl or the radical of the formula

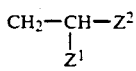

where $Z^1$ is hydrogen or methyl and $Z^2$ is a group which is detachable under alkaline reaction conditions, the radical A being linked to the benzene ring meta or para to the $CH_2$-$SO_3H$ group.

Examples of U were mentioned above.

The novel benzyl compounds, which are useful intermediates for synthesizing the novel double attachment reactive dyes, can be obtained in a conventional manner, for example as described in EP-A-307 817.

For instance, a compound of the formula XXIV

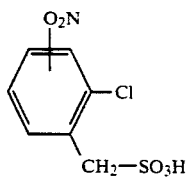 (XXIV)

can be reacted with a thioalkanol, e.g. 2-thioethanol or 1-methyl-2-thioethanol.

By reducing the nitro group to an amino group and oxidizing the sulfur atom to a sulfone group, in either order, and then esterifying for example with chlorosulfuric acid, it is possible to arrive at the benzyl sulfone of the formula XXV

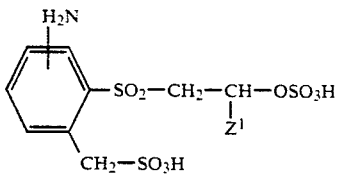 (XXV)

where $Z^1$ is as defined above.

Compounds of the formula XXIV can be obtained for example by reacting a benzyl chloride of the formula XXVI

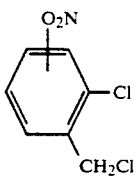 (XXVI)

with an alkali metal sulfite.

Instead of the sulfuric ester group, the other radicals which are detachable under alkaline conditions can likewise be introduced in a conventional manner.

The reactive dyes of the formula I are prepared for example by reacting a suitable organic dye or a suitable dye precursor and the fiber-reactive compound of the formula XXVII

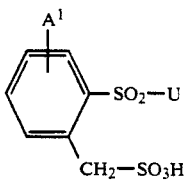 (XXVII)

where

U is as defined above and
$A^1$ is the radical

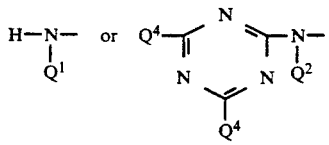

where $Q^1$, $Q^2$ and $Q^4$ are each as defined above, and, if dye precursors have been used, converting the resulting intermediates into the desired dyes by a conventional method.

If the compound X-H is a coupling component, the dyes according to the present invention are obtained for example by diazotizing the fiber-reactive system of the formula XXVIII

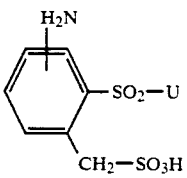 (XXVIII)

where U is as defined above, in a conventional manner and coupling it to the coupling component X-H.

The novel reactive dyes of the formula I are advantageous for dyeing or printing hydroxyl- or nitrogen-containing organic substrates. Such substrates are for example leather and fiber material which predominantly contains natural or synthetic polyamides or natural or regenerated cellulose. The novel dyes are preferable for dyeing and printing textile material based on wool or in particular cotton. Suitable dyeing methods are the known forms of reactive dyeing, in particular exhaust dyeing at 40°-80° C. and cold pad-batch dyeing. The novel dyes are notable for high yield and high wet fastness.

The Examples which follow, in which percentages are by weight, unless otherwise stated, further illustrate the invention.

In the table examples, the abbreviations E-1 to E-4 have the following meanings:

E-1: 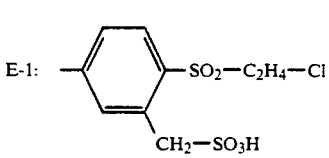

-continued

E-2: 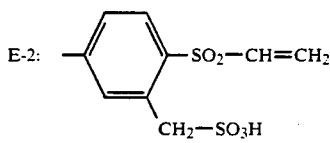

E-3: 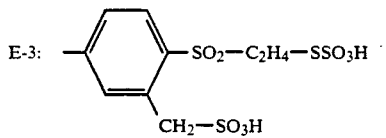

E-4: 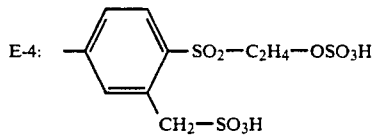

EXAMPLE 1

A solution of 31.4 g of 4-(2'-chloroethylsulfonyl)-3-hydroxysulfonylmethylaniline in 500 ml of water was diazotized with 60 ml of 5N hydrochloric acid and 30 ml of 3.33N NaNO$_2$ solution at 0°-5° C. and admixed with a neutral aqueous solution of 30.2 g of 1-hydroxynaphthalene-3,6-disulfonic acid. Sodium bicarbonate was sprinkled in to set a pH of 5-6. After the coupling had ended, the dye was salted out with potassium chloride and gently dried under reduced pressure. It dyes cotton in light-fast orange shades and conforms to the formula

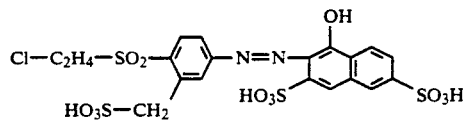

Further dyes according to the present invention which were obtained in a similar manner are listed in Table 1:

TABLE 1

| | | E—N=N—K | |
|---|---|---|---|
| Ex. No. | E | K | Hue on cotton |
| 2 | E-1 | ![](CH₃, CH₂SO₃H, O, N-C₂H₅, OH) | greenish yellow |
| 3 | E-4 | ![](CH₃, CONH₂, O, N-C₂H₅, OH) | greenish yellow |
| 4 | E-3 | ![](CH₃, O, N-CH₃, OH) | greenish yellow |
| 5 | E-2 | ![](H₃C, N=N, CH₃, HO, SO₃H) | yellow |
| 6 | E-3 | ![](HO₂C, N=N, HO, SO₃H) | yellow |

TABLE 1-continued

| Ex. No. | E | K (E—N=N—K) | Hue on cotton |
|---|---|---|---|
| 7 | E-1 | benzene with SO₃H, NH₂, NH—CO—CH₃ | yellowish orange |
| 8 | E-1 | benzene with SO₃H, NH₂, NH—CO—NH₂ | yellowish orange |
| 9 | E-3 | benzene with SO₃H, NH₂, NH—CO—CH₃ | yellowish orange |
| 10 | E-2 | naphthalene with HO, HO₃S, SO₃H | orange |
| 11 | E-1 | naphthalene with HO, SO₃H, SO₃H | orange |
| 12 | E-2 | naphthalene with HO, SO₃H, HO₃S | orange |
| 13 | E-1 | naphthalene with HO, SO₃H | reddish orange |
| 14 | E-3 | naphthalene with HO, SO₃H | reddish orange |
| 15 | E-1 | pyrimidine with HO, OH, HO, N, N | greenish yellow |

TABLE 1-continued

| Ex. No. | E | E—N=N—K<br>K | Hue on cotton |
|---|---|---|---|
| 16 | E-1 | ![structure with H2N, N, morpholine, HO] | yellow |
| 17 | E-1 | ![structure with CO2H, HO, N, OH] | greenish yellow |
| 18 | E-1 | ![naphthalene with H2N, SO3H, HO3S] | reddish orange |

EXAMPLE 19

31.4 g of 4-(2'-chloroethylsulfonyl)-3-hydroxysulfonylmethylaniline in 500 ml of water were diazotized at 0°–5° C. in the presence of hydrochloric acid and admixed with a neutral aqueous solution of 42.4 g of 1-benzoylamino-8-hydroxynaphthalene-4,6-disulfonic acid. The coupline was completed at pH 6–6.5 by sprinkling in sodium bicarbonate, and the dye formed was salted out with sodium chloride and gently dried under reduced pressure. It dyes cotton in a brilliant red shade having good fastness properties and conforms to the formula

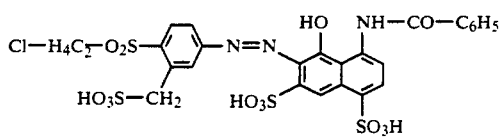

Further dyes which were obtained in a similar manner are listed in Table 2.

TABLE 2

| Ex. No. | E | E—N=N—K<br>K | Hue on cotton |
|---|---|---|---|
| 20 | E-1 | ![naphthalene with HO, NH—COCH3, HO3S, SO3H] | red |
| 21 | E-3 | ![naphthalene with HO, NH—COC6H5, HO3S, SO3H] | red |
| 22 | E-1 | ![naphthalene with HO, NH—CO—NH—C6H5, HO3S, SO3H] | bluish red |

TABLE 2-continued $$E-N=N-K$$

| Ex. No. | E | K | Hue on cotton |
|---|---|---|---|
| 23 | E-1 | 8-hydroxy-7-methyl-1-(chloroacetylamino)naphthalene-3,6-disulfonic acid residue (HO, NH—CO—CH₂—Cl; HO₃S, SO₃H) | red |
| 24 | E-1 | 8-hydroxy-7-methyl-1-(propionylamino)naphthalene-3,6-disulfonic acid residue (HO, NH—CO—C₂H₅; HO₃S, SO₃H) | red |
| 25 | E-1 | 1-hydroxy-2-methyl-6-(3-chloropropionylamino)naphthalene-3-sulfonic acid residue (HO; HO₃S; NH—CO—CH₂—CH₂—Cl) | orange |
| 26 | E-2 | 1-hydroxy-2-methyl-6-acetylaminonaphthalene-3-sulfonic acid residue (HO; HO₃S; NH—COCH₃) | orange |
| 27 | E-1 | 1-hydroxy-2-methyl-6-(β-sulfopropionylamino)naphthalene-3-sulfonic acid residue (HO; HO₃S; NH—COCH₂CH₂SO₃H) | orange |

EXAMPLE 28

15.7 g of 4-(2'-chloroethylsulfonyl)-3-hydroxysulfonylmethylaniline were dissolved in 250 ml of water and diazotized at 0° C. in the presence of hydrochloric acid. This solution was added dropwise to a suspension of 16 g of 1-amino-8-hydroxynaphthalene-3,6-disulfonic acid in 100 ml of water at pH 1. The mixture was stirred overnight and filtered, 15.7 g of 4-(2'-chloroethylsulfonyl)3-hydroxysulfonylmethylaniline (diazotized as described above) were added dropwise, and coupling was carried out with sodium bicarbonate at pH 5.5–6. The mixture was stirred overnight and the dye was salted out with KCl and gently dried. It has the formula

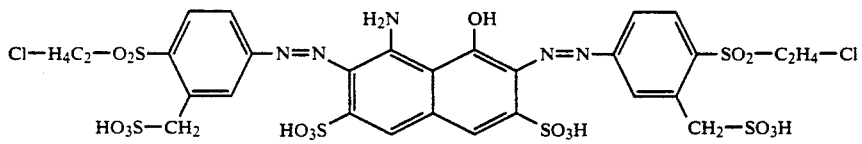

and dyes cotton in a navy shade having good fastness properties.

EXAMPLE 29

8.7 g of sulfanilic acid were diazotized in 200 ml of $H_2O$ at 0° C. in the presence of hydrochloric acid. A suspension of 13.7 g of 1-amino-8-hydroxynaphthalene-3,6-disulfonic acid (Na salt) in 100 ml of water was added dropwise. The pH was 1.5 . The mixture was stirred overnight at room temperature.

The diazonium salt, prepared by diazotization of 15.7 g of 4-(2'-chloroethylsulfonyl)-3-hydroxymethylaniline with sodium nitrile in the presence of hydrochloric acid, was then added dropwise at 10° C.

The pH was maintained with sodium bicarbonate at 5.5–6 for 2 hours, and the dye was salted out with potassium chloride, filtered off with suction and dried to give a black powder which dyes cotton in a navy shade of good light fastness. The dye conforms to the formula

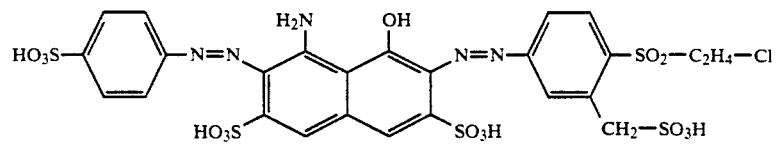

Further dyes according to the present invention which were obtained in a similar manner are listed in Table 3.

TABLE 3

Structure: Naphthalene core with $H_2N$ and $OH$ substituents, two azo groups $D^1-N=N-$ and $-N=N-D^2$ at positions adjacent, with $HO_3S$ groups, and positions labeled 3 and 4 bearing $SO_3H$.

| Ex. No. | $D^1$ | $D^2$ | Position 3 or 4 | Hue on cotton |
|---|---|---|---|---|
| 30 | 4-sulfophenyl ($HO_3S-C_6H_4-$) | E-1 | 4 | navy |
| 31 | 2,5-disulfophenyl (benzene with $SO_3$ and $HO_3S$) | E-2 | 3 | navy |
| 32 | naphthyl with $SO_3H$ groups (1,5-disulfo-2-naphthyl type) | E-1 | 3 | navy |
| 33 | E-2 | E-2 | 3 | navy |
| 34 | E-3 | E-3 | 3 | navy |
| 35 | E-1 | triazinyl group: 4-sulfo-3-methylanilino — triazine (with Cl) — NH-phenyl-$SO_3H$ | 3 | navy |
| 36 | E-1 | trichloropyrimidinyl-NH-(4-sulfo-3-methylphenyl) group | 3 | navy |

TABLE 3-continued
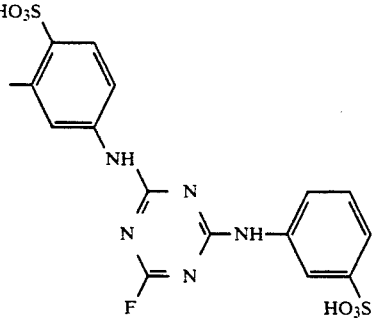
| Ex. No. | D¹ | D² | Position 3 or 4 | Hue on cotton |
|---|---|---|---|---|
| 37 | E-1 | 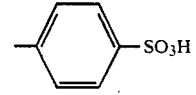 | 3 | navy |
| 38 | E-1 | 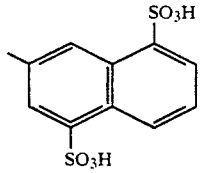 | 3 | navy |
| 39 | E-1 | 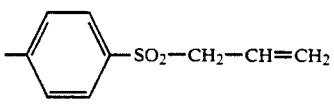 | 4 | navy |
| 40 | E-1 | —⟨⟩—SO₂—CH₂—CH=CH₂ | 3 | navy |
| 41 | E-1 | —⟨⟩—SO₂—C₂H₄—OSO₃H | 3 | navy |
| 42 | E-1 | 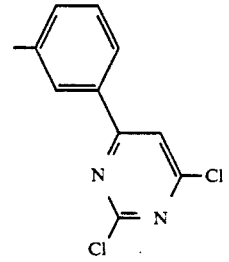 | 3 | navy |

TABLE 3-continued
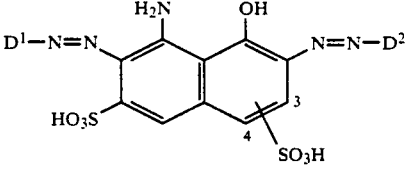
| Ex. No. | D¹ | D² | Position 3 or 4 | Hue on cotton |
|---|---|---|---|---|
| 43 | E-2 | 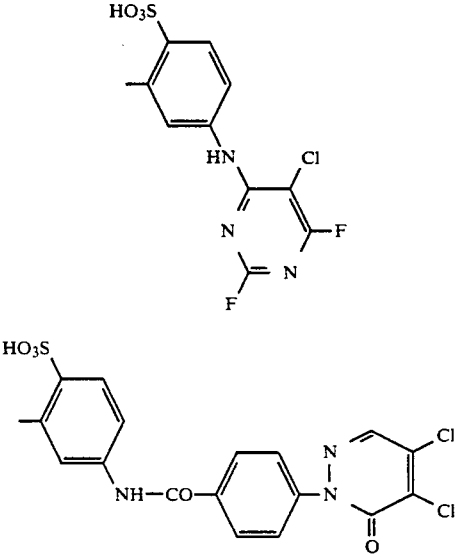 | 3 | navy |
| 44 | E-1 | 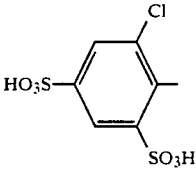 | 3 | navy |
| 45 | 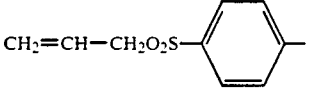 | E-1 | 3 | reddish navy |
| 46 | $CH_2=CH-CH_2O_2S$—⟨ ⟩— | E-1 | 3 | navy |
| 47 | $HO_3SOH_4C_2O_2S$—⟨ ⟩— | E-1 | 3 | navy |
| 48 | 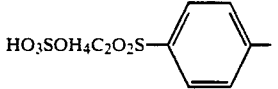 | E-1 | 3 | navy |
| 49 | $HO_3SOH_4C_2HNO_2S$—⟨ ⟩— | E-1 | 3 | navy |
| 50 | E-1 | —⟨ ⟩—$SO_2NHC_2H_4OSO_3H$ | 3 | navy |

EXAMPLE 51

25.4 g of the secondary condensation product of aniline-3-sulfonic acid, 2,4,6-trifluoro-1,3,5-triazine and 2-amino-5-hydroxynaphthalene-7-sulfonic acid in a neutral solution in 800 ml of water were admixed at 0°–5° C. with the diazonium salt prepared by diazotization of 15.7 g of 4-(2'-hydroxyethylsulfonyl)-3-hydroxysulfonylmethylaniline with sodium nitrite in the presence of hydrochloric acid in 300 ml of water. Sodium bicarbonate was added to set a pH of from 5 to 6, and the dye obtained was salted out with sodium chloride. Following gentle drying, the dye was in the form of a reddish orange powder which dyes cotton in a brilliant orange shade. The dye conforms to the formula

EXAMPLE 52

A neutral solution of 55.2 g of the secondary condensation product of 1-amino-8-hydroxynaphthalene-3,6-disulfonic acid, cyanuric chloride and N-ethylaniline in 700 ml of water was admixed with the diazonium salt prepared by diazotization of 31.4 g of 4-(2'-chloroethylsulfonyl)-3-hydroxysulfonylmethylaniline with sodium nitrite in the presence of hydrochloric acid, in 500 ml of water. The coupling was completed at pH 5–6 by the addition of sodium bicarbonate. The dye formed was salted out with sodium chloride and gently dried. It conforms to the formula

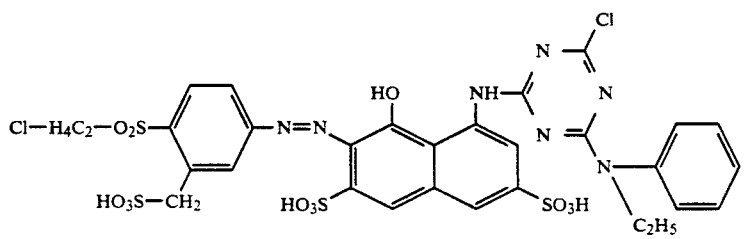

and dyes cotton in a brilliant red shade having good fastness properties.

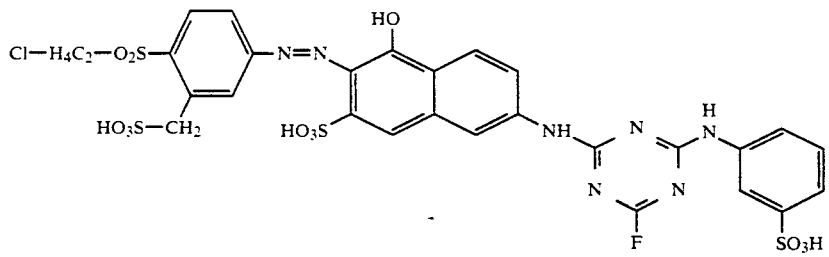

The dyes listed in Table 4 were obtained in a similar manner to Examples 51 and 52.

TABLE 4

E—N=N—K with triazine ring substituted by X and R

| Ex. No. | E | K | X | R | Hue on cotton |
|---|---|---|---|---|---|
| 53 | E-1 | OH / NH— naphthalene with HO₃S and SO₃H | Cl | OCH₃ | red |
| 54 | E-1 | OH / NH— naphthalene with HO₃S and SO₃H | F | 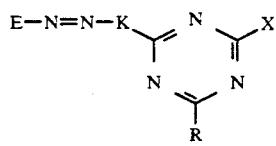 | red |

TABLE 4-continued $$E-N=N-K\underset{\underset{R}{\overset{N}{\|}}}{\overset{N}{\underset{\|}{\bigtriangleup}}}X$$

| Ex. No. | E | K | X | R | Hue on cotton |
|---|---|---|---|---|---|
| 55 | E-1 | 4-amino-5-hydroxy-6-methyl-naphthalene-2,7-disulfonic acid (NH- at 4-position) | Cl | OCH$_2$CH$_2$OCH$_3$ | red |
| 56 | E-1 | 1-hydroxy-2-methyl-7-(NH-)-naphthalene-3-sulfonic acid | Cl | 3-sulfophenylamino | orange |
| 57 | E-1 | 3-carboxy-1-(2-sulfo-5-amino-phenyl)-4-methyl-5-hydroxypyrazole (azo) | Cl | 3-sulfophenylamino | yellow |
| 58 | E-2 | 3-carboxy-1-(3-aminophenyl)-4-methyl-5-hydroxypyrazole (azo) | Cl | 3-sulfophenylamino | yellow |
| 59 | E-1 | 3-carboxy-1-(3-aminophenyl)-4-methyl-5-hydroxypyrazole (azo) | F | 3-sulfophenylamino | yellow |
| 60 | E-1 | 1-(3-aminopropyl)-3-carbamoyl-4-methyl-5-methyl-6-hydroxy-2-pyridone | Cl | 3-sulfophenylamino | greenish yellow |
| 61 | E-1 | 2-amino-4-(NH-)-5-methyl-benzenesulfonic acid | Cl | 4-sulfophenylamino | yellowish orange |
| 62 | E-1 | 2-amino-4-(NH-)-5-methyl-benzenesulfonic acid | F | 4-sulfophenylamino | yellowish orange |

TABLE 4-continued

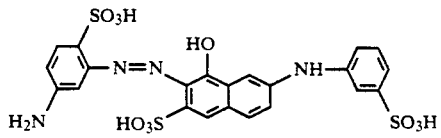

| Ex. No. | E | K | X | R | Hue on cotton |
|---|---|---|---|---|---|
| 63 | E-2 | ![structure: aniline with SO3H, NH2, NH-] | Cl | ![structure: NH-phenyl-SO3H] | yellowish orange |

EXAMPLE 64

A neutral aqueous solution of 31.4 g of 4-(2'-chloroethylsulfonyl)-3-hydroxysulfonylmethylaniline in 500 ml of water was admixed with a suspension of 19.3 g of cyanuric chloride in 250 ml of ice-water and stirred at 0°-5° C. for 2.5 hours during which a pH of 5-6 was maintained by the addition of sodium bicarbonate. Following filtration, the suspension was added to a stirred solution of 16.9 g of 1,3-diaminobenzene-4-sulfonic acid in 100 ml of water at 40° C. and pH 5-6, and the mixture was maintained at 35°-40° C. and a pH of 3-4 for 2 hours.

After the reaction had ended, the product was diazotized at 0°-5° C. by the addition of 30 ml of 3.33N aqueous sodium nitrite solution and 60 ml of 5N hydrochloric acid and coupled onto 27.6 g of 1,4-dimethyl-3-hydroxysulfonylmethyl-6-hydroxypyrid-2-one. The dye obtained was salted out with sodium chloride and gently dried under reduced pressure. It dyes cotton in a brilliant, fast, greenish yellow shade and conforms to the formula

EXAMPLE 65

33 g of the sodium salt of the dye of the formula

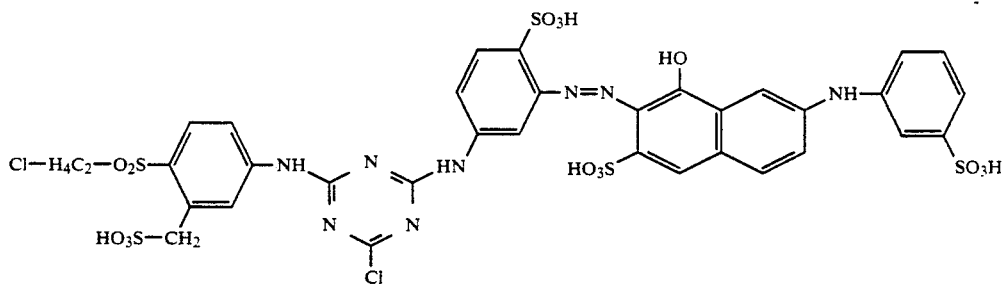

were dissolved in water at pH 6 and 40° C., 31.6 g of the condensation product of cyanuric chloride and 4-(2'-chloroethylsulfonyl)-3-hydroxysulfonylmethylaniline described in Example 64, dissolved in 1,000 ml of water were added, and the mixture was stirred at 40° C. for a further 2 hours during which a pH of 5-6 was maintained by sprinkling in sodium bicarbonate. The dye, obtained by precipitation with potassium chloride and gentle drying, dyes cotton in a brown shade and conforms to the formula The dyes described in Table 5 are obtained in a similar manner.

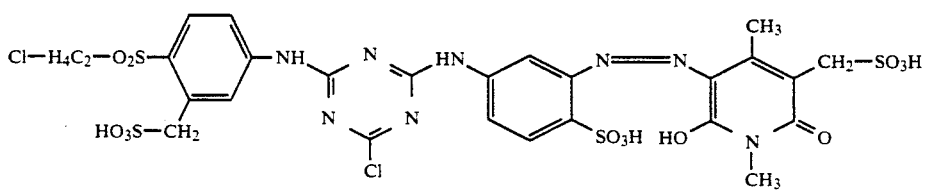

TABLE 5

(structure shown at top: triazine with X, NH-D-N=N-K, and E-NH substituents)

| Ex. No. | E | X | D | K | Hue on cotton |
|---|---|---|---|---|---|
| 66 | E-1 | Cl | benzene with SO₃H (2,4-substituted) | 4-hydroxy-5-(NH—COC₆H₅)-3-methyl-naphthalene-2,7-disulfonic acid derivative (HO, NH—COC₆H₅, HO₃S, SO₃H) | red |
| 67 | E-1 | F | benzene with SO₃H (2,4-substituted) | 4-hydroxy-5-(NH—COC₆H₅)-3-methyl-naphthalene-2,7-disulfonic acid derivative | red |
| 68 | E-1 | Cl | benzene with SO₃H (2,4-substituted) | 4-hydroxy-5-(NH—COCH₃)-3-methyl-naphthalene-2,7-disulfonic acid derivative | red |
| 69 | E-1 | Cl | benzene with SO₃H (2,4-substituted) | 4-hydroxy-5-(NH—COC₂H₅)-3-methyl-naphthalene-2,7-disulfonic acid derivative | red |
| 70 | E-1 | Cl | benzene with SO₃H (2,4-substituted) | naphthalene(HO, HO₃S, SO₃H)-NH-triazine(Cl, N(C₆H₅)(C₂H₅)) | red |
| 71 | E-1 | Cl | benzene with SO₃H (2,4-substituted) | HO₂C—C=...—N=N—C₆H₄—SO₃H (pyrazolone: HO₂C, CH₃, OH, N=N-phenyl-4-SO₃H) | yellow |
| 72 | E-1 | Cl | benzene with SO₃H (2,4-substituted) | HO₂C—pyrazolone—N=N—(2-Cl,5-SO₃H-phenyl) | yellow |

TABLE 5-continued
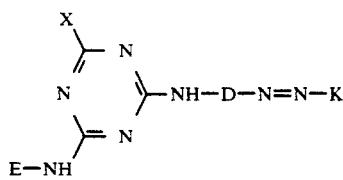
| Ex. No. | E | X | D | K | Hue on cotton |
|---|---|---|---|---|---|
| 73 | E-1 | Cl | 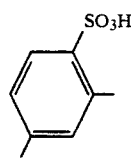 | 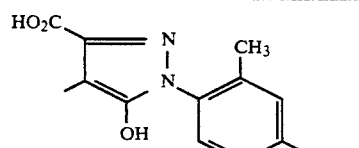 | yellow |
| 74 | E-1 | Cl | 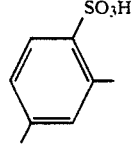 | 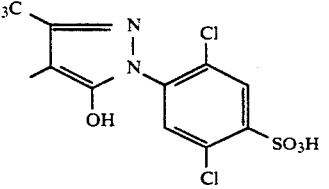 | yellow |
| 75 | E-1 | Cl | 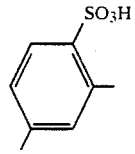 | 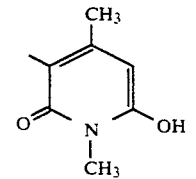 | greenish yellow |
| 76 | E-1 | Cl | 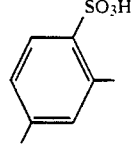 | 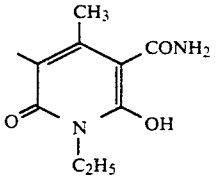 | greenish yellow |
| 77 | E-1 | Cl | 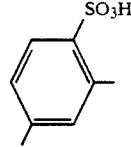 | 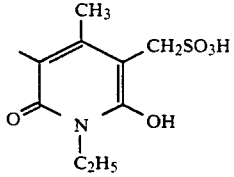 | greenish yellow |
| 78 | E-1 | Cl | 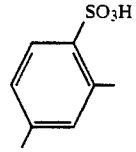 | 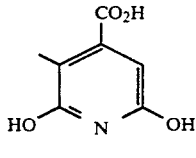 | greenish yellow |
| 79 | E-1 | Cl | 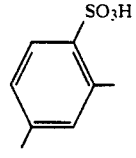 | 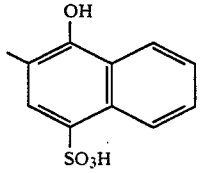 | reddish orange |

TABLE 5-continued
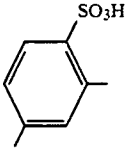
| Ex. No. | E | X | D | K | Hue on cotton |
|---|---|---|---|---|---|
| 80 | E-1 | Cl | 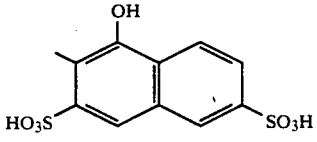 | 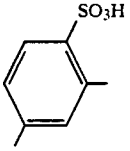 | orange |
| 81 | E-1 | Cl | 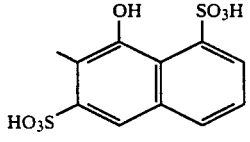 | 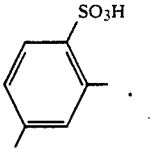 | orange |
| 82 | E-1 | Cl | 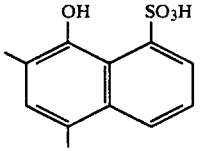 | 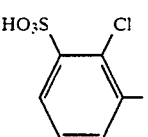 | reddish orange |
| 83 | E-1 | Cl | 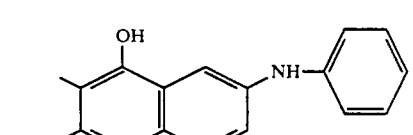 | 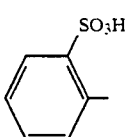 | brown |
| 84 | E-1 | Cl | 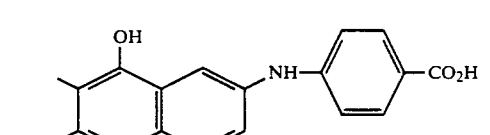 | 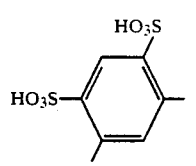 | brown |
| 85 | E-1 | Cl | 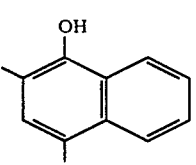 | 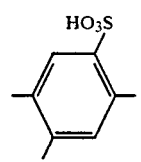 | reddish orange |
| 86 | E-1 | Cl | 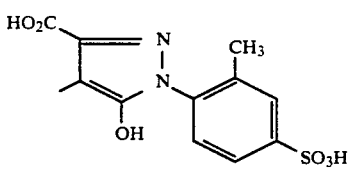 | 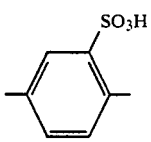 | yellowish orange |
| 87 | E-1 | Cl | 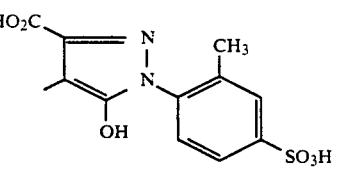 | | yellowish orange |

TABLE 5-continued

Structure:
X—C(=N)—N=C(NH—D—N=N—K)—N=C(NH—E)— (triazine with E—NH and NH—D—N=N—K substituents)

| Ex. No. | E | X | D | K | Hue on cotton |
|---|---|---|---|---|---|
| 88 | E-1 | Cl | 2,5-dimethylbenzenesulfonic acid (SO₃H) | 4-hydroxy-3-methyl-2,7-naphthalenedisulfonic acid | red |
| 89 | E-1 | Cl | 2,5-dimethylbenzenesulfonic acid | 4-hydroxy-1-methyl-3-carbamoyl-6-hydroxy-pyridone | yellowish orange |
| 90 | E-1 | Cl | 2,5-dimethylbenzenesulfonic acid | 2,6-dihydroxy-3-methyl-pyridine-5-carboxylic acid | yellowish orange |
| 91 | E-1 | Cl | 2,5-dimethylbenzenesulfonic acid | 1-hydroxy-2-methyl-3-sulfo-6-acetylamino-naphthalene | orange |
| 92 | E-1 | F | 2,5-dimethylbenzenesulfonic acid | 1-hydroxy-2-methyl-3-sulfo-6-acetylamino-naphthalene | orange |
| 93 | E-1 | Cl | 2,5-dimethylbenzenesulfonic acid | 1-hydroxy-2-methyl-3-sulfo-6-acetylamino-naphthalene | orange |
| 94 | E-1 | Cl | 2,5-dimethylbenzenesulfonic acid | 1-hydroxy-2-methyl-3-amino-6-(3-chloropropanoylamino)-naphthalene | orange |
| 95 | E-1 | Cl | 2,5-dimethylbenzenesulfonic acid | 1-hydroxy-2-methyl-3-sulfo-6-acetylamino-naphthalene | red |

TABLE 5-continued

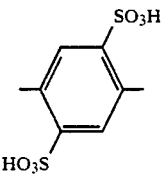

| Ex. No. | E | X | D | K | Hue on cotton |
|---|---|---|---|---|---|
| 96 | E-2 | Cl | 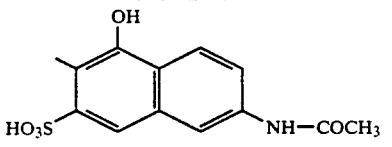 | 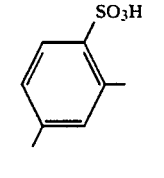 | red |
| 97 | E-1 | Cl | 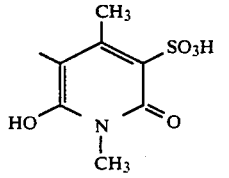 | 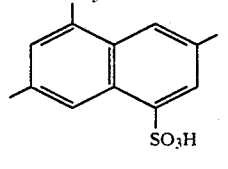 | greenish yellow |
| 98 | E-1 | Cl | 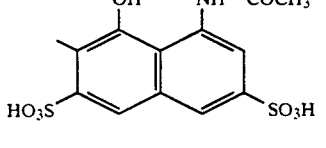 | 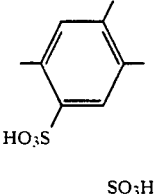 | bluish red |
| 99 | E-1 | Cl | 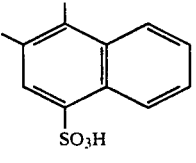 | 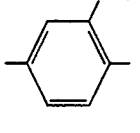 | red |
| 100 | E-1 | Cl | 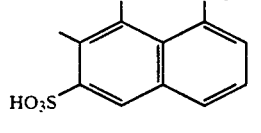 | 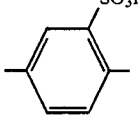 | red |
| 101 | E-1 | Cl | | 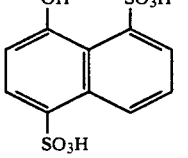 | red |

EXAMPLE 102

27.7 g of the aminoazo dye obtained by coupling diazotized 2-aminonaphthalene-3,6,8-trisulfonic acid onto 3-aminophenylurea were dissolved in 250 ml of water under neutral conditions and admixed at 40° C. with a neutral aqueous solution (prepared as in Example 64) of 21.4 g of the condensation product of cyanuric chloride and 4-(2'-chloroethylsulfonyl)-3-hydroxysulfonylmethylaniline in 1,000 ml of water, and the mixture was stirred at 40° C. for 2 hours while a pH of 5-6 was maintained by sprinkling in sodium bicarbonate. As soon as free amino groups were no longer detectable by thin layer chromatography, the dye was salted out with potassium chloride and gently dried under reduced pressure. It conforms to the formula

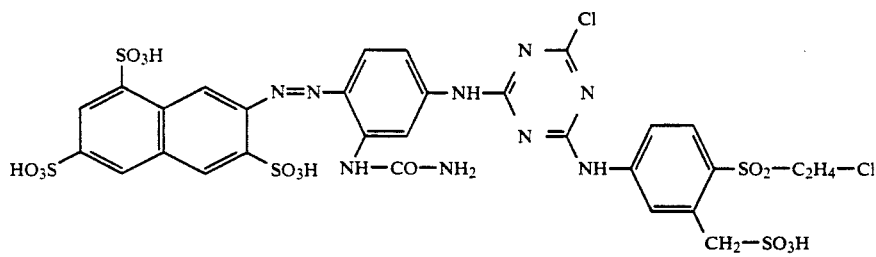

and dyes cotton in a fast, yellowish orange shade having good fastness properties.

EXAMPLE 103

The neutral aqueous solution of 21.4 g of the primary condensation product of cyanuric chloride and 4-(2'-chloroethylsulfonyl)-3-hydroxysulfonylmethylaniline described in Example 64 was admixed with 15 g of 1-amino-8-hydroxynaphthalene-3,6-disulfonic acid, and the mixture was stirred at 30° C. for 2 hours while a pH of 5-6 was maintained by the addition of sodium bicarbonate. The mixture was cooled to 0°-5° C. with ice, 8.7 g of diazotized aniline-2-sulfonic acid were added, and the coupling was completed at pH 5-6 by the addition of sodium bicarbonate. The resulting dye has the structural formula

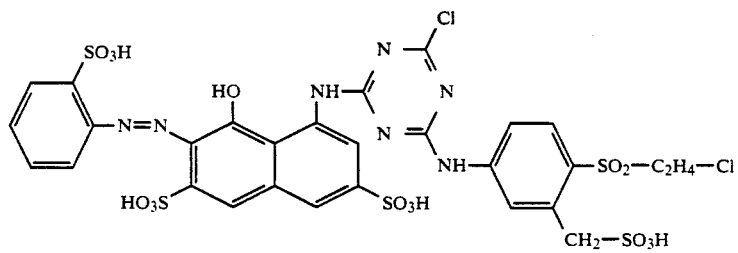

and dyes cotton in a fast, brilliant red shade.

The dyes listed in Table 6 are obtained in a similar manner.

TABLE 6

| Ex. No. | D | K | X | E | Hue on cotton |
|---|---|---|---|---|---|
| 104 | 2-SO₃H-phenyl | 1-OH-8-NH-, 3-SO₃H, 6-SO₃H naphthyl | Cl | E-1 | red |
| 105 | 2-SO₃H-phenyl | 1-OH-8-NH-, 3-SO₃H, 6-SO₃H naphthyl | F | E-1 | red |
| 106 | 2-SO₃H-4-OCH₃-phenyl | 1-OH-8-NH-, 3-SO₃H, 6-SO₃H naphthyl | Cl | E-1 | bordeaux |
| 107 | 2-SO₃H-5-CH₃-phenyl | 1-OH-8-NH-, 3-SO₃H, 6-SO₃H naphthyl | Cl | E-1 | bluish red |

TABLE 6-continued

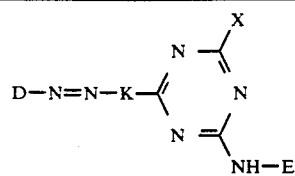

| Ex. No. | D | K | X | E | Hue on cotton |
|---|---|---|---|---|---|
| 108 | 4-HO₂C-C₆H₄- | 5-hydroxy-8-amino-naphthalene-2,7-disulfonic acid (6-methyl) | Cl | E-1 | bluish red |
| 109 | 4-(CH₂=CH-CH₂-SO₂)-C₆H₄- | 5-hydroxy-8-amino-naphthalene-2,7-disulfonic acid (6-methyl) | Cl | E-1 | red |
| 110 | 4-(HO₃SO-CH₂-CH₂-SO₂)-C₆H₄- | 5-hydroxy-8-amino-naphthalene-2,7-disulfonic acid (6-methyl) | Cl | E-1 | red |
| 111 | 2-methyl-naphthalene-1,5-disulfonic acid | 5-hydroxy-8-amino-naphthalene-2,7-disulfonic acid (6-methyl) | Cl | E-1 | bluish red |
| 112 | C₆H₅- | 4-hydroxy-5-amino-naphthalene-2,8-disulfonic acid (6-methyl) | Cl | E-1 | red |
| 113 | 2-HO₃S-C₆H₄- | 8-hydroxy-3-amino-naphthalene-6-sulfonic acid (7-methyl) | Cl | E-1 | orange |
| 114 | 4-methoxy-2-sulfo-phenyl | 8-hydroxy-3-amino-naphthalene-6-sulfonic acid (7-methyl) | Cl | E-1 | orange |
| 115 | 5-methyl-2,4-disulfo-phenyl | 8-hydroxy-3-amino-naphthalene-6-sulfonic acid (7-methyl) | Cl | E-1 | orange |

TABLE 6-continued
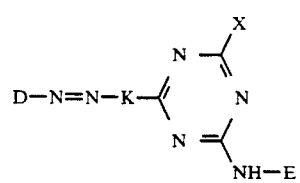
| Ex. No. | D | K | X | E | Hue on cotton |
|---|---|---|---|---|---|
| 116 | 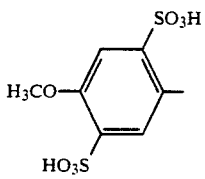 | 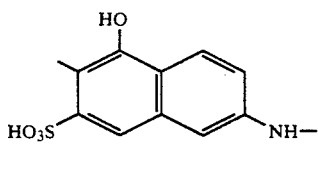 | Cl | E-1 | orange |
| 117 | 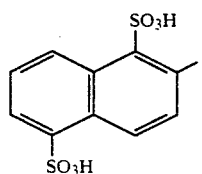 | 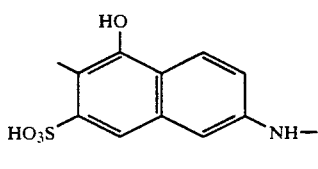 | Cl | E-1 | orange |
| 118 | 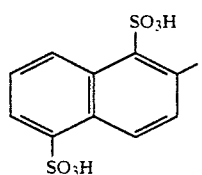 | 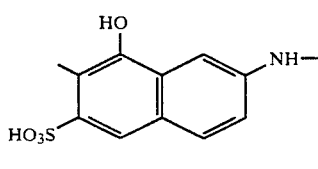 | Cl | E-1 | yellowish red |
| 119 | 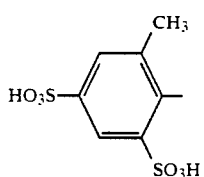 | 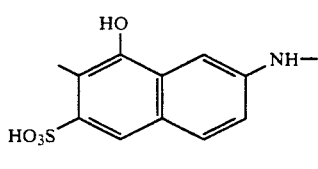 | Cl | E-1 | yellowish red |
| 120 | 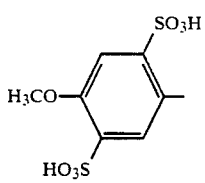 | 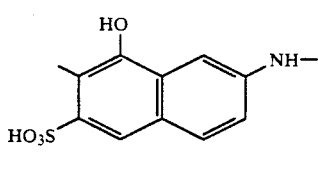 | Cl | E-1 | yellowish red |
| 121 | 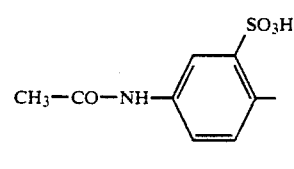 | 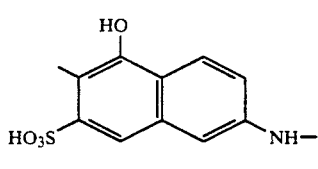 | Cl | E-1 | red |
| 122 | 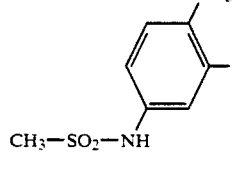 | 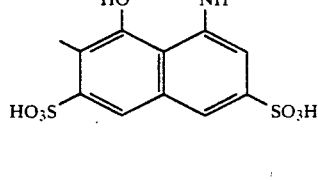 | Cl | E-1 | red |

TABLE 6-continued $$D-N=N-K \begin{array}{c} \diagup N \diagdown \\ \diagdown N \diagup \end{array} \begin{array}{c} X \\ | \\ N \\ | \\ NH-E \end{array}$$

| Ex. No. | D | K | X | E | Hue on cotton |
|---|---|---|---|---|---|
| 123 | [chlorotriazine linked via NH to methyl-phenyl-SO₃H and NH to phenyl-SO₃H (meta)] | [8-amino-1-hydroxy-naphthalene-3,6-disulfonic acid, 2-methyl] | Cl | E-1 | red |
| 124 | [chlorotriazine with E¹-NH and NH-methyl-phenyl-SO₃H] | [8-amino-1-hydroxy-naphthalene-3,6-disulfonic acid, 2-methyl] | Cl | E-1 | red |
| 125 | [chlorotriazine with E¹-NH and NH-phenyl(SO₃H)-methyl] | [6-amino-1-hydroxy-naphthalene-3-sulfonic acid, 2-methyl] | Cl | E-1 | red |
| 126 | [chlorotriazine with NH-phenyl-SO₃H and NH-phenyl(SO₃H)₂-methyl] | [6-amino-1-hydroxy-naphthalene-3-sulfonic acid, 2-methyl] | Cl | E-1 | red |
| 127 | [naphthalene-1,5,7-trisulfonic acid, 3-methyl] | [methyl-phenyl with NH- and NH-COCH₃] | Cl | E-1 | yellowish orange |
| 128 | [naphthalene-1,5,7-trisulfonic acid, 3-methyl] | [methyl-phenyl with NH- and NH-COCH₃] | F | E-1 | yellowish orange |
| 129 | [naphthalene-1,5,7-trisulfonic acid, 3-methyl] | [methyl-phenyl with NH- and NH-CONH₂] | F | E-1 | yellowish orange |

TABLE 6-continued
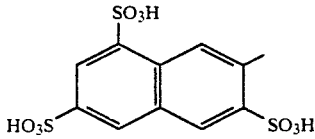
| Ex. No. | D | K | X | E | Hue on cotton |
|---|---|---|---|---|---|
| 130 | 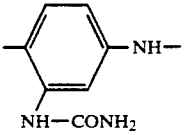 | 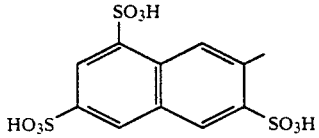 | Cl | E-2 | yellowish orange |
| 131 | 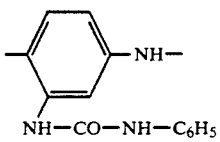 | 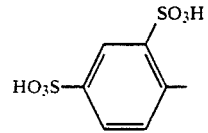 | Cl | E-1 | yellowish orange |
| 132 | 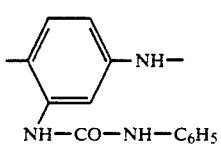 | 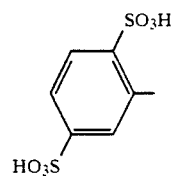 | Cl | E-1 | yellow |
| 133 | 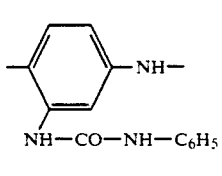 | 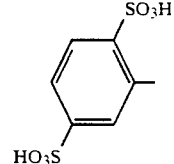 | Cl | E-1 | yellow |
| 134 | 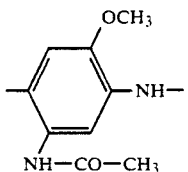 | 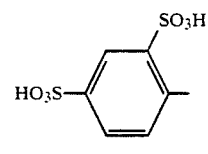 | Cl | E-1 | yellowish orange |
| 135 | 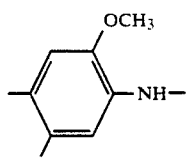 | 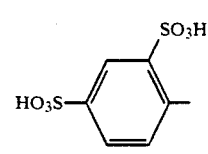 | Cl | E-1 | yellowish orange |
| 136 | 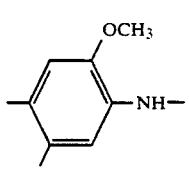 | 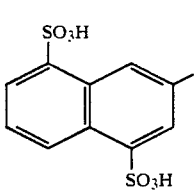 | Cl | E-1 | yellowish orange |
| 137 | 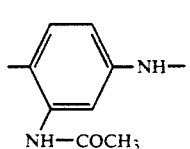 | | Cl | E-1 | yellowish orange |

TABLE 6-continued

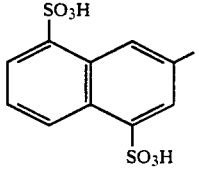

| Ex. No. | D | K | X | E | Hue on cotton |
|---|---|---|---|---|---|
| 138 | 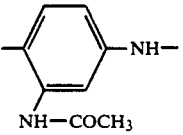 (naphthalene with SO₃H, SO₃H, CH₃) | 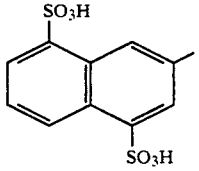 (phenyl with —NH—, NH—COCH₃) | F | E-1 | yellowish orange |
| 139 | (naphthalene with SO₃H, SO₃H, CH₃) | (phenyl with OCH₃, —NH—, H₃N) | Cl | E-1 | yellowish orange |

EXAMPLE 140

8.7 g of sulfanilic acid were diazotized in 250 ml of water in the presence of hydrochloric acid. A suspension of 13.7 g of 1-amino-8-hydroxynaphthalene-3,6-disulfonic acid in 100 ml of water was added dropwise, and the mixture was stirred at room temperature and pH 1.5 for 12 hours. After cooling to 10° C., a diazo component was added which was obtained by diazotizing 56.4 g of the secondary condensation product of 4-(2'-chloroethylsulfonyl)-3-hydroxysulfonylmethylaniline, cyanuric chloride and 1,3-phenylenediamine-4-sulfonic acid in 750 ml of water in the presence of hydrochloric acid.

The reaction was completed overnight at pH 5.5-6 by the addition of sodium bicarbonate. The dye was salted out with 200 g of sodium chloride and dried. It has the formula

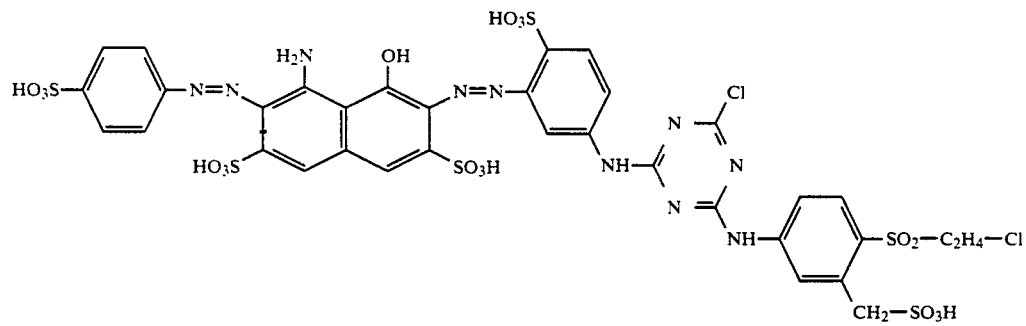

and dyes cotton in a fast, navy shade.

EXAMPLE 141

Example 140 was repeated, except that 1-amino-8-hydroxynaphthalene-4,6-disulfonic acid was used in place of 1-amino-8-hydroxynaphthalene-3,6-disulfonic acid. A dye having similar properties was obtained.

Table 7 contains further examples of dyes prepared in a similar manner to Example 140.

TABLE 7
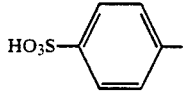
| Ex. No. | D¹ | Position 3/4 | D² | X | E | Hue on cotton |
|---|---|---|---|---|---|---|
| 142 | 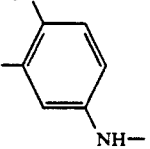 | 3 | 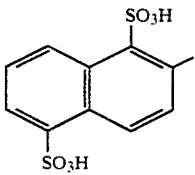 | F | E-1 | navy |
| 143 | 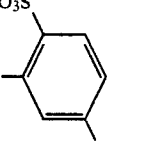 | 3 | 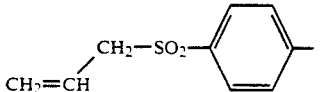 | Cl | E-1 | navy |
| 144 | 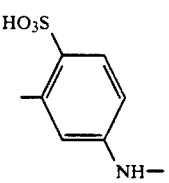 | 4 | 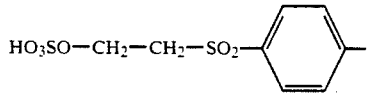 | Cl | E-1 | navy |
| 145 | 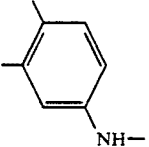 | 3 | 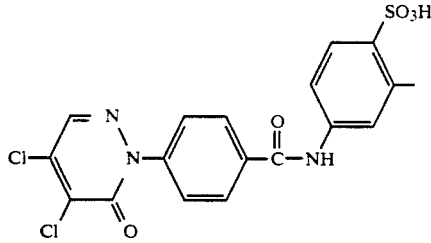 | Cl | E-1 | navy |
| 146 | 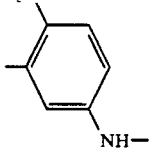 | 3 | 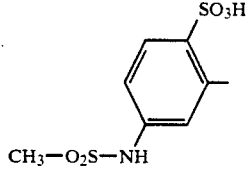 | Cl | E-1 | navy |
| 147 | 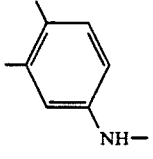 | 3 | 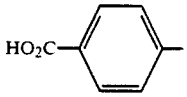 | Cl | E-1 | navy |
| 148 | 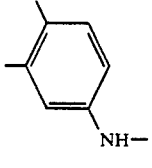 | 3 | 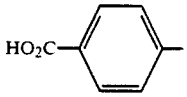 | Cl | E-1 | navy |

TABLE 7-continued

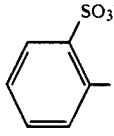

| Ex. No. | D¹ | Position 3/4 | D² | X | E | Hue on cotton |
|---|---|---|---|---|---|---|
| 149 | [2-SO₃H-phenyl] | 3 | [4-SO₃H-phenyl-3-NH-] | Cl | E-1 | navy |
| 150 | [3-HO₃S-phenyl] | 3 | [4-SO₃H-phenyl-3-NH-] | Cl | E-1 | navy |

EXAMPLE 151

A solution of 28.2 g of the secondary condensation product of 1,3-phenylenediamine-4-sulfonic acid, cyanuric chloride and 4-(2'-chloroethylsulfonyl)-3-hydroxysulfonylmethylaniline in 750 ml of water, prepared and diazotized as described in Example 140, was admixed at 0°-5° C. with 15.9 g of 1-amino-8-hydroxynaphthalene-3,6-disulfonic acid, suspended in 100 ml of water. A pH of 2.5-3 was maintained with sodium formate. The mixture was stirred at room temperature for 12 hours, the diazonium salt prepared by diazotization of 8.7 g of aniline-4-sulfonic acid in the presence of hydrochloric acid in 200 ml of water was then added at 10° C., and the pH was maintained with sodium bicarbonate at 6-6.5. Salting out with sodium chloride brought down a dye of the formula

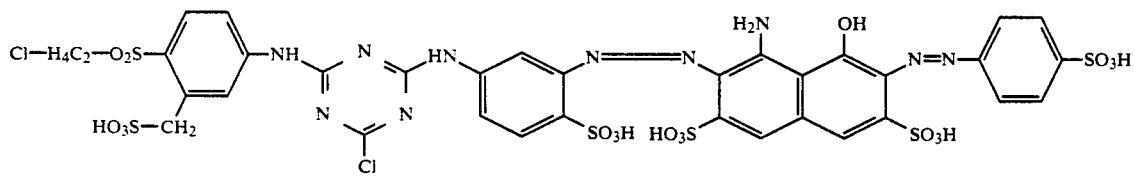

The dyes listed in Table 8 are obtained in a similar manner.

TABLE 8

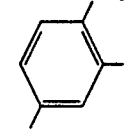

| Ex. No. | E | X | D¹ | Position 3/4 | D² | Hue on cotton |
|---|---|---|---|---|---|---|
| 152 | E-1 | Cl | [2-SO₃H-phenyl] | 3 | [4-SO₃H-phenyl-3-NH-C(=N)-N=C(Cl)-N=C(NH-E¹)-] | navy |

TABLE 8-continued

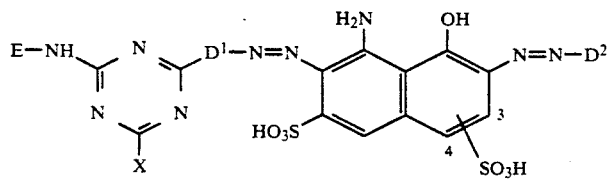

| Ex. No. | E | X | D¹ | Position 3/4 | D² | Hue on cotton |
|---|---|---|---|---|---|---|
| 153 | E-1 | Cl | 2-methyl-4-amino-benzenesulfonic acid (SO₃H ortho, NH para) | 3 | 2-methylbenzenesulfonic acid | navy |
| 154 | E-1 | Cl | 2-methyl-4-amino-benzenesulfonic acid | 3 | 3-sulfophenyl | navy |
| 155 | E-2 | Cl | 2-methyl-4-amino-benzenesulfonic acid | 3 | phenyl-NH-triazine(Cl)(NH-E²) with SO₃H | navy |
| 156 | E-1 | Cl | 2-methyl-4-amino-benzenesulfonic acid | 4 | 4-sulfophenyl | navy |
| 157 | E-1 | Cl | 2-methyl-4-amino-benzenesulfonic acid | 3 | $-C_6H_4-SO_2-CH_2-CH=CH_2$ | navy |
| 158 | E-1 | Cl | 2-methyl-4-amino-benzenesulfonic acid | 4 | $-C_6H_4-SO_2-C_2H_4-OSO_3H$ | navy |

EXAMPLE 159

38.6 g of the known dye of the formula

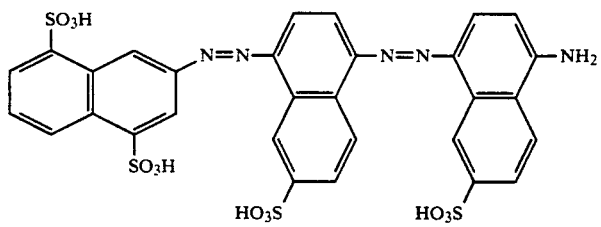

in 400 ml of water at pH 7 were admixed at 40° C. with 21.4 g of the primary condensation product of cyanuric chloride and 4-(2'-chloroethylsulfonyl)-3-hydroxysulfonylmethylaniline in 500 ml of water prepared as in Example 64. The mixture was stirred at 40° C. and pH 5-6 until free amino groups were no longer detectable by thin layer chromatography. The dye obtained on salting out with potassium chloride conforms to the formula

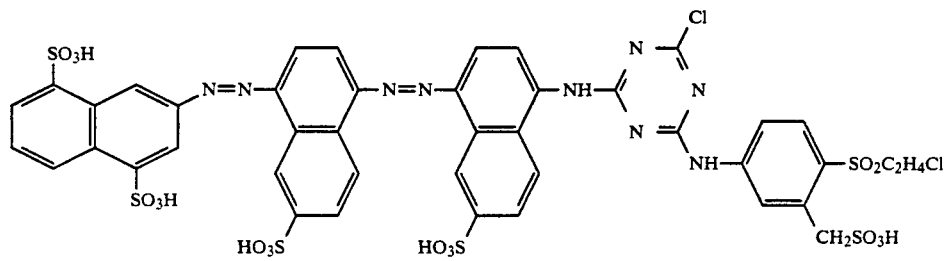

and dyes cotton in a reddish brown shade.

Table 9 contains dyes obtained in a similar manner.

TABLE 9

D—N=N—K¹—N=N—K²—NH—C(N)=N—C(X)=N—C(NH—E)

| Ex. No. | D | K¹ | K² | X | E | Hue on cotton |
|---|---|---|---|---|---|---|
| 160 | 2,4-disulfophenyl (SO₃H, HO₃S) | naphthyl-HO₃S | naphthyl-HO₃S | Cl | E-1 | reddish brown |
| 161 | 2,4-disulfophenyl | naphthyl-HO₃S | naphthyl-SO₃H | Cl | E-1 | reddish brown |
| 162 | naphthyl-1,5-disulfo (SO₃H, HO₃S, SO₃H) | naphthyl | naphthyl-SO₃H | Cl | E-1 | reddish brown |

TABLE 9-continued $$D-N=N-K^1-N=N-K^2-NH-\overset{N}{\underset{N}{\bigtriangleup}}-NH-E$$
(with X on the triazine)

| Ex. No. | D | $K^1$ | $K^2$ | X | E | Hue on cotton |
|---|---|---|---|---|---|---|
| 163 | naphthalene-2,5,7-trisulfonic acid (SO₃H, HO₃S, SO₃H) | 2,5-dimethyl phenyl | 6-sulfonaphthyl | Cl | E-1 | yellowish brown |
| 164 | naphthalene-1,5-disulfonic acid-3-yl | 2,5-dimethyl phenyl | 8-sulfonaphthyl | Cl | E-2 | yellowish brown |
| 165 | naphthalene-1,3,5-trisulfonic acid-7-yl | 6-sulfonaphthyl | 2,5-dimethyl phenyl | F | E-1 | yellowish brown |
| 166 | naphthalene-1,3,5-trisulfonic acid-7-yl | naphthyl | 6-sulfonaphthyl | Cl | E-1 | reddish brown |
| 167 | E¹ | 6-sulfonaphthyl | 6-sulfonaphthyl | Cl | 2-methyl-4-sulfophenyl-SO₃H | reddish brown |
| 168 | 2-methyl-4-sulfophenyl | 6-sulfonaphthyl | sulfonaphthyl | Cl | E-1 | reddish brown |

TABLE 9-continued $$D-N=N-K^1-N=N-K^2-NH\underset{\underset{X}{\overset{N}{\bigwedge}}}{\overset{N}{\bigwedge}}NH-E$$

| Ex. No. | D | K¹ | K² | X | E | Hue on cotton |
|---|---|---|---|---|---|---|
| 169 | ![D169: naphthalene with SO₃H at 1-position, HO₃S at another position, methyl] | ![naphthalene with HO₃S] | ![naphthalene with HO₃S] | Cl | E-1 | reddish brown |
| 170 | ![benzene with SO₃H, CH₃SO₂NH, methyl] | ![naphthalene with HO₃S] | ![naphthalene with HO₃S] | Cl | E-1 | reddish brown |

EXAMPLE 171

64.8 g of the known dye of the formula

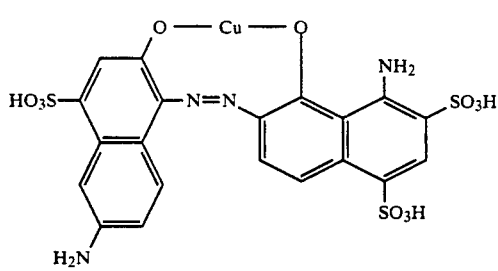

were suspended in 700 ml of water. 21.4 g of the primary condensation product of cyanuric chloride and 4-(2'-chloroethylsulfonyl)-3-hydroxysulfonylmethylaniline described in Example 64 were added dissolved in 800 ml of water at pH 5.5- and 40° C. in the course of 2 hours, and the reaction mixture was maintained at pH 5.5–6 and 40°–45° C. for a further 30 minutes. After the reaction had ended, the dye was salted out with sodium chloride, filtered off and dried under reduced pressure. It conforms to the formula

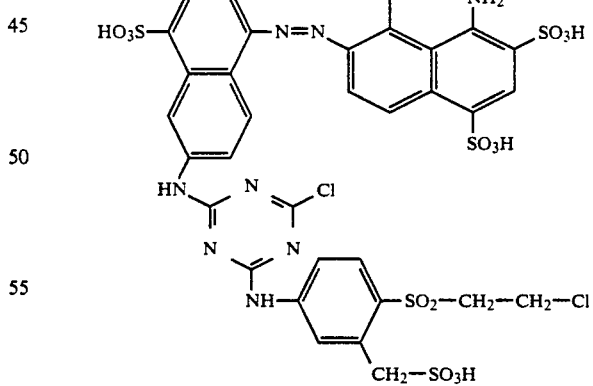

and dyes cotton in a fast blue shade.

EXAMPLE 172

A suspension of 75 g of the known dichlorotriazine dye of the formula

EXAMPLE 173

The method described in Example 172 can also be used to prepare the dye of the formula

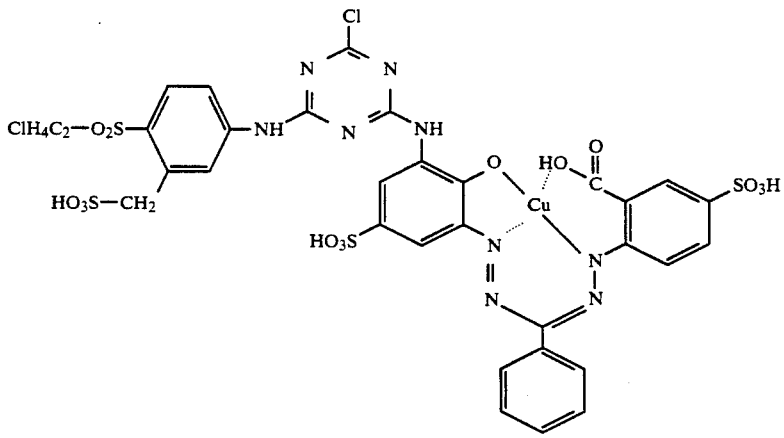

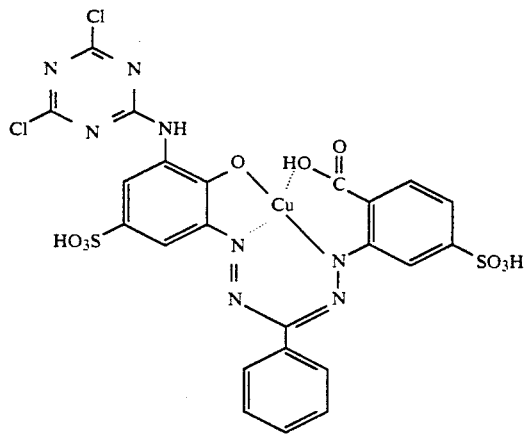

in 600 ml of water was admixed at neutral pH with a solution of 49 g of 4-(2'-chloroethylsulfonyl)-3-hydroxysulfonylmethylaniline in 600 ml of water. The suspension was heated to 40°–45° C. and a neutral pH was maintained by the addition of NaHCO$_3$. After 2.5 hours the product dye conforming to the formula

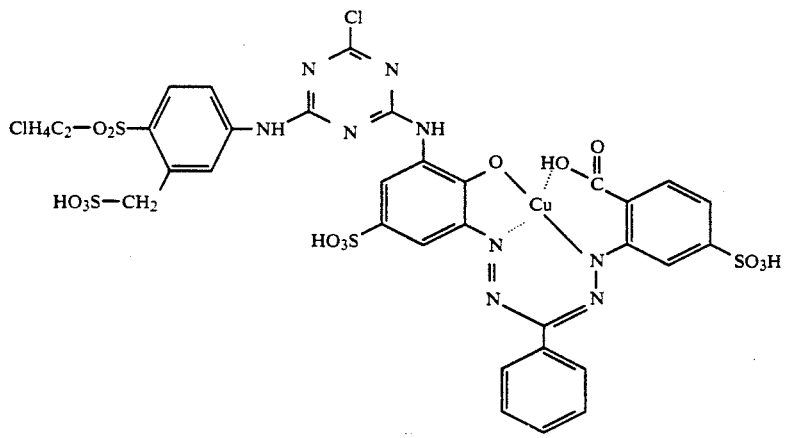

was salted out with 250 g of sodium chloride, filtered off and dried. The dark blue dye powder obtained dyes cotton in a sky blue shade. The dyeings are light- and wet-fast and they show remarkable stability to oxidative effects.

EXAMPLE 174

43.4 g of 88% strength 1-amino-4-bromoanthraquinone-2-sulfonic acid, 34.5 g of the amine of the formula

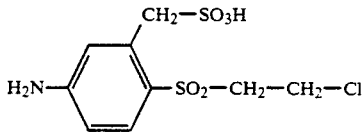

1.5 g of copper powder, 0.75 g of copper(II) sulfate and 50.4 g of sodium bicarbonate were heated at 65°–70° C. for 120 hours. After the reaction had ended (thin layer chromatography), the mixture was filtered hot and the filtrate was brought to pH 1 with concentrated hydrochloric acid. The oily residue was crystallized at 0°–5° C. by stirring with 100 ml of ethanol to extract the impurities, and the crystalline product was isolated, washed with ethanol and dried, leaving 45 g of the compound of the formula

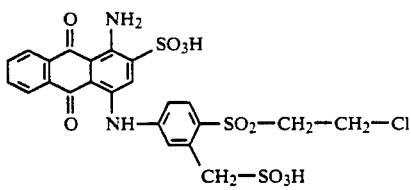

The same method was used to obtain the compounds of the formula

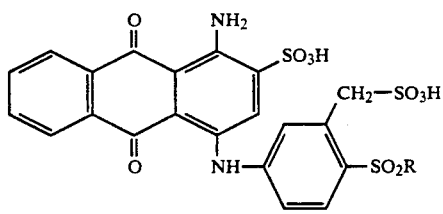

listed in Table 10.

TABLE 10

| Ex. No. | R |
|---|---|
| 175 | CH=CH$_2$ |
| 176 | CH$_2$CH$_2$OH |
| 177 | CH$_2$CH$_2$SSO$_3$H |

EXAMPLE 178

10 g of the Example 174 compound of the formula

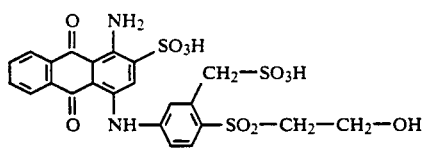

was stirred in 40 g of chlorosulfonic acid at 20°–25° C. for 3 hours. The melt was poured into 400 g of ice-water, and sodium bicarbonate was added to adjust the pH to 5. The solution was spray-dried to isolate a product which in addition to salt contained the dye of the formula

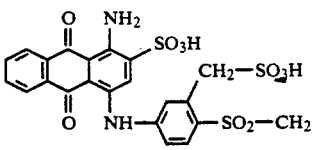

On cotton it produces brilliant blue dyeings having good fastness properties.

EXAMPLE 179

12.2 g of 1-amino-4-(3'-amino-4'-hydroxysulfonylphenylamino)-2-hydroxysulfonylanthraquinone were stirred in 250 ml of water adjusted to pH 6.5 with sodium hydroxide solution. A suspension of 4.61 g of cyanuric chloride in 100 g of ice-water was added at 0°–5° C. The mixture was stirred at 0°–5° C. and pH 6.5 until the reaction had ended, which took about 2 hours.

Following the addition of 8.6 g of 4-(2'-chloroethylsulfonyl)-3-hydroxysulfonylmethylaniline, the temperature was raised to 35° C., and the mixture was stirred at that temperature for 2 hours.

After cooling to room temperature, the dye was salted out with 100 g of sodium chloride, filtered off with suction and dried.

It dyes cotton in a blue shade having good fastness properties and conforms to the formula

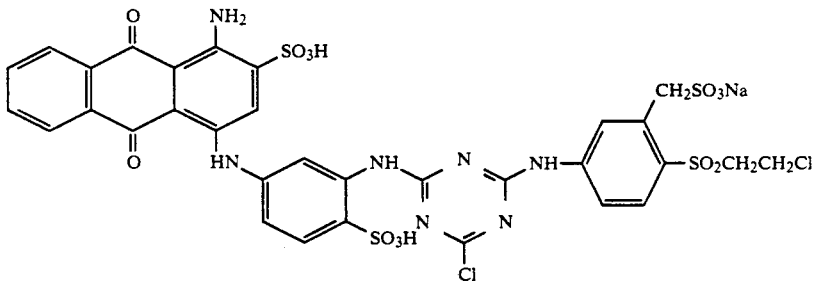

EXAMPLE 180

A further dye having similar properties was obtained on using instead of 1-amino-4-(3'-amino-4-hydroxysulfonylphenylamino)-2-hydroxysulfonylanthraquinone 13.2 g of 1-amino-4-(3'-amino-5'-hydroxysulfonyl-2',4',6'-trimethylphenylamino)-2-hydroxysulfonylanthraquinone.

It conforms to the formula

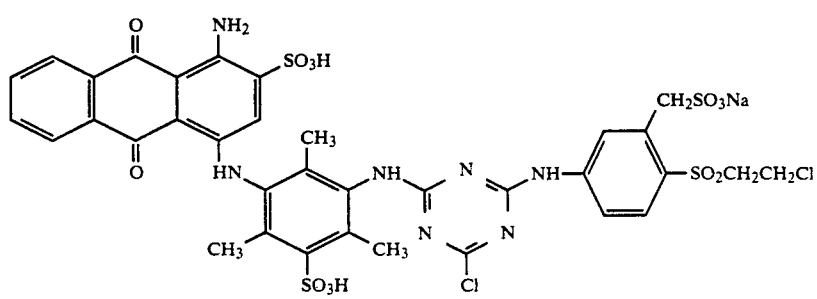

The same method was used to obtain the compounds of the formula

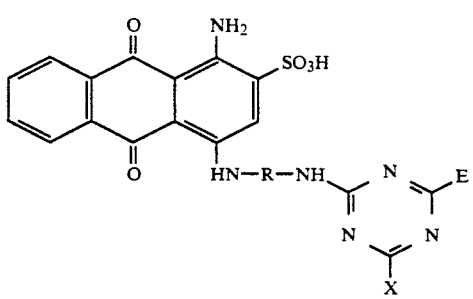

listed below in Table 11.

TABLE 11

| Ex. No. | R | X | E | Hue on cotton |
|---|---|---|---|---|
| 181 | 3-methyl-4-sulfophenyl | Cl | E-2 | |
| 182 | 2-sulfophenyl | F | E-2 | |
| 183 | 3-methyl-4-sulfophenyl | F | E-1 | |
| 184 | 3-methyl-4-sulfophenyl | Cl | E-3 | |
| 185 | 3-methyl-4-sulfophenyl | F | E-3 | |
| 186 | 3-methyl-4-sulfophenyl | Cl | E-4 | |

TABLE 11-continued

| Ex. No. | R | X | E | Hue on cotton |
|---|---|---|---|---|
| 187 | 3-methyl-4-sulfophenyl | F | E-4 | |
| 188 | 2,4,6-trimethyl-3-sulfophenyl | F | E-1 | |
| 189 | 2,4,6-trimethyl-3-sulfophenyl | Cl | E-2 | |
| 190 | 2,4,6-trimethyl-3-sulfophenyl | F | E-2 | |
| 191 | 2,4,6-trimethyl-3-sulfophenyl | Cl | E-3 | |
| 192 | 2,4,6-trimethyl-3-sulfophenyl | F | E-3 | |
| 193 | 2,4,6-trimethyl-3-sulfophenyl | Cl | E-4 | |
| 194 | 2,4,6-trimethyl-3-sulfophenyl | F | E-4 | |

EXAMPLE 195

19.1 g of the compound of the formula

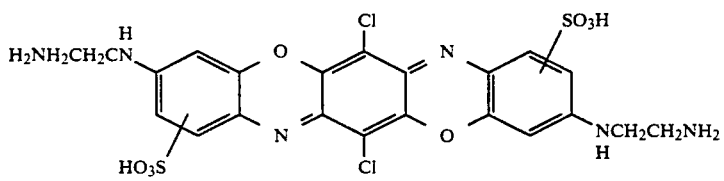

were stirred into 1,000 g of water, and the mixture was adjusted to pH 10 with sodium hydroxide solution. The resulting solution was added dropwise at 40°-50° C. to a hot solution of the condensation product of 11.1 g of cyanuric chloride with 18.8 g of 4-(2'-chloroethylsulfonyl)-3-hydroxysulfonylmethylaniline adjusted to pH 6-8. The mixture was stirred at 60° C. at pH 6.5-7 until the reaction had ended, which took about 1 hour. After cooling to room temperature, the dye was salted out with 500 g of NaCl, filtered off with suction and dried. It dyes cotton in a brilliant blue shade having good fastness properties and conforms to the formula

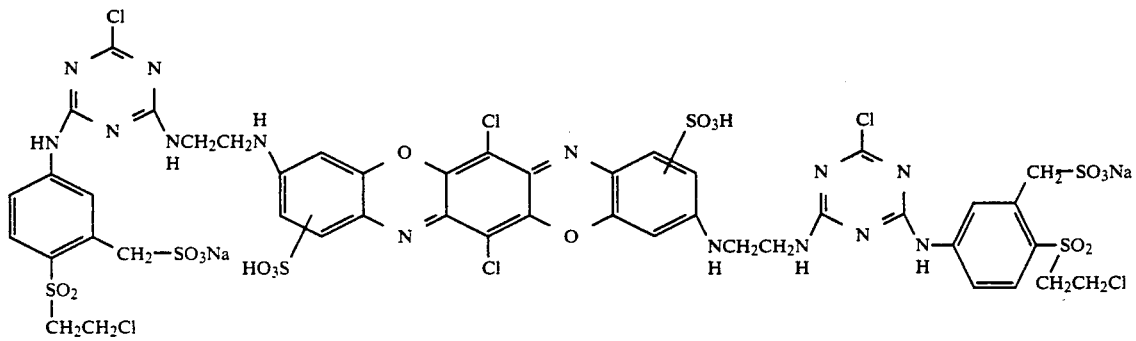

Further dyes obtained in a similar manner are given in Table 12.

TABLE 12

| Ex. | Y | X | R | E | Hue on cotton |
|---|---|---|---|---|---|
| 196 | HN−CH(CH₃)−NH | SO₃H | Cl | E-1 | blue |
| 197 | HN−CH₂CH₂−NH | SO₃H | F | E-1 | blue |
| 198 | HN−(CH₂)₃−NH | SO₃H | Cl | E-1 | blue |
| 199 | HN−C₆H₄−NH | SO₃H | Cl | E-1 | blue |
| 200 | HN−CH₂CH₂−NH | SO₂C₂H₄OSO₃H | Cl | E-1 | blue |
| 201 | O−CH₂CH₂−NH | SO₃H | Cl | E-1 | red |
| 202 | O−C₆H₄−NH | SO₃H | Cl | E-1 | red |
| 203 | HN−CH₂CH₂−NH | SO₃H | Cl | E-2 | blue |

TABLE 12-continued

[Structure: E-NH-triazine(R)-Y-phenyl(X)-O-dichloroquinone-N=...-N=...-O-phenyl(X)-Y-triazine(R)-NH-E]

| Ex. | Y | X | R | E | Hue on cotton |
|---|---|---|---|---|---|
| 204 | HN-CH₂CH₂-NH | SO₃H | F | E-2 | blue |
| 205 | HN-CH₂-CH(CH₃)-NH | SO₃H | Cl | E-2 | blue |
| 206 | HN-(CH₂)₃-NH | SO₃H | Cl | E-2 | blue |
| 207 | HN-C₆H₄-NH (para) | SO₃H | Cl | E-2 | blue |
| 208 | HN-CH₂CH₂-NH | SO₂C₂H₄OSO₃H | Cl | E-2 | blue |
| 209 | O-CH₂CH₂-NH | SO₃H | Cl | E-2 | red |
| 210 | O-C₆H₄-NH (para) | SO₃H | Cl | E-2 | red |
| 211 | HN-CH₂CH₂-NH | SO₃H | Cl | E-3 | blue |
| 212 | HN-CH₂CH₂-NH | SO₃H | F | E-3 | blue |
| 213 | HN-CH₂-CH(CH₃)-NH | SO₃H | Cl | E-3 | blue |
| 214 | HN-(CH₂)₃-NH | SO₃H | Cl | E-3 | blue |
| 215 | HN-C₆H₄-NH (para) | SO₃H | Cl | E-3 | blue |
| 216 | HN-CH₂CH₂-NH | SO₂C₂H₄OSO₃H | Cl | E-3 | blue |
| 217 | O-CH₂CH₂-NH | SO₃H | Cl | E-3 | red |
| 218 | O-C₆H₄-NH (para) | SO₃H | Cl | E-3 | red |
| 219 | HN-CH₂CH₂-NH | SO₃H | Cl | E-4 | blue |
| 220 | HN-CH₂CH₂-NH | SO₃H | F | E-4 | blue |
| 221 | HN-CH₂-CH(CH₃)-NH | SO₃H | Cl | E-4 | blue |

TABLE 12-continued

|  |  |  |  |  |  |
|---|---|---|---|---|---|

(structure shown at top of table with substituents E, N, H, Y, X, R, Cl, O, N)

| Ex. | Y | X | R | E | Hue on cotton |
|---|---|---|---|---|---|
| 222 | HN—(CH₂)₃—NH | SO₃H | Cl | E-4 | blue |
| 223 | HN—C₆H₄—NH | SO₃H | Cl | E-4 | blue |
| 224 | HN—CH₂CH₂—NH | SO₂C₂H₄OSO₃H | Cl | E-4 | blue |
| 225 | O—CH₂CH₂—NH | SO₃H | Cl | E-4 | red |
| 226 | O—C₆H₄—NH | SO₃H | Cl | E-4 | red |

EXAMPLE 227

97 g of copper phthalocyaninetetrasulfonyl chloride were added in the form of a moist press cake to a neutral solution of 28.4 g of 4-(2'-chloroethylsulfonyl)-3-hydroxysulfonylmethylaniline in 200 ml of water at 5°–10° C. The mixture was stirred at 20°–25° C. for 12 hours while the pH was maintained at 6.5–7.3 by the addition of 10% strength sodium carbonate solution. The mixture was then filtered with suction and the filter residue was dried, leaving 47 g of the dye of the formula

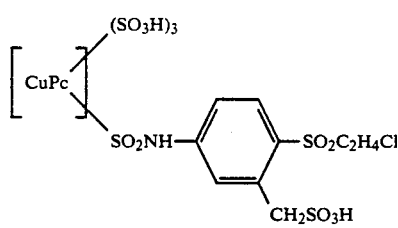

which contained 2.7% of NaCl. It dyes cotton in a greenish blue shade.

EXAMPLE 228

97 g of copper phthalocyaninetetrasulfonyl chloride were suspended in 750 ml of water at 0°–5° C. 20.5 g of monoacetylethylenediamine were added and the pH was maintained at 7.3–7.5 with 10% strength sodium carbonate solution. Following 12 hours at 20°–25° C., the pH was increased to 10 by the addition of sodium hydroxide solution, and the mixture was stirred at 95° C. for one hour. Concentrated hydrochloric acid was added to bring down a precipitate. It was filtered off with suction, washed with approximately 2% strength hydrochloric acid and resuspended in 500 ml of water. The pH was adjusted with sodium hydroxide solution to 7.0–7.2, and 21.2 g of cyanuric chloride were added at 0°–5° C. The pH was maintained at 6.5–7.0 by the dropwise addition of sodium carbonate solution. After 3 hours 29 g of 4-(2'-chloroethylsulfonyl)-3-hydroxysulfonylmethylaniline were added and the temperature was raised to 35°–40° C. The dye solution was spray-dried. 185 g were isolated of the dye of the formula

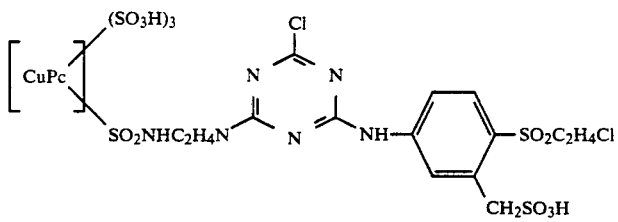

It dyes cotton in a greenish blue shade.

EXAMPLE 229

97 g of copper phthalocyaninetetrasulfonyl chloride were suspended in 600 ml of water at 0°–5° C. 41 g of N-monoacetyl-m-phenylenediamine were added and the pH was maintained at 6.8–7.0 by the addition of 10% strength sodium carbonate solution. 12 g of 25% strength ammonia solution and 16 g of sodium acetate were then added, and the temperature was raised to 50° C. in the course of 3 hours and the pH was maintained at 7.0. 250 g of concentrated hydrochloric acid were added and the temperature was raised to 90°–95° C.

After 4 hours, the mixture was cooled down and the resulting precipitate was filtered off with suction and washed until neutral. Without drying, the precipitate was resuspended in 750 ml of water and admixed at pH 7.0 and 0°–5° C. with 19.4 g of cyanuric chloride. The pH was maintained at 6.5–7.0 by the addition of sodium carbonate solution. After 3 hours 29 g of 4-(2'-chloroethylsulfonyl)-3-hydroxysulfonylmethylaniline were added and the temperature was raised to 35°–40° C. The dye solution was spray-dried. 260 g were isolated of the dye of the formula

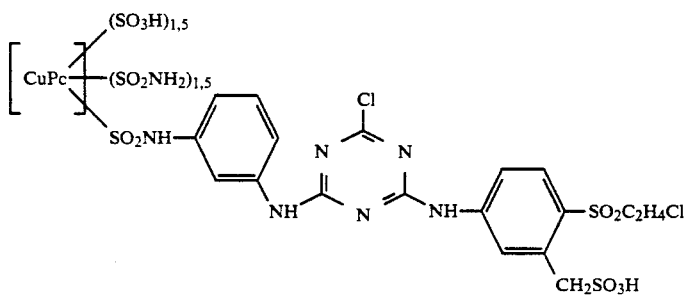

which dyes cotton in a greenish blue shade.

EXAMPLE 230

768 g of 2-chloro-5-nitrobenzyl chloride and 470 g of $Na_2SO_3$ were suspended in 3.5 ml of water. The temperature was raised to 85°–90° C. and the mixture was stirred at that temperature for 10 hours. After cooling to room temperature, the precipitated product was filtered off, washed with a little cold water and acetone and then dried at 50° C. under reduced pressure.

1,815 g were obtained of a crystalline product of the following constitution:

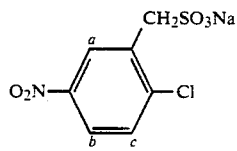

$^1$H-NMR: 4.05 (s, $CH_2$), 7.70 (d, aromatic -$H^c$), 8.10 (dd, aromatic -$H^b$), 8.40 (d, aromatic $H^a$).

EXAMPLE 231

360 g of the product obtained in Example 230 were dissolved in 750 ml of N,N-dimethylformamide and admixed at room temperature first with 182 g of potash and then (with ice cooling) with 128.2 g of 2-mercaptoethanol.

The mixture was stirred at 0°–5° C. for 2 hours, then warmed to 30°–35° C. and stirred for a further 16 hours.

After cooling, the precipitated product was filtered off, washed with methanol and dried at 40° C. under reduced pressure. 490 g were obtained of a saltcontaining product of the following constitution:

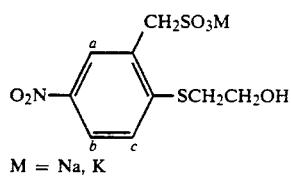

M = Na, K $^1$H-NMR: 3.15 (t, $CH_2$), 3.60 (t, $CH_2$), 3.95 (s, $CH_2$), 5.10 (s, OH), 7.60 (d, aromatic -$H^c$), 8.08 (dd, aromatic -$H^b$), 8.30 (d, aromatic -$H^a$).

EXAMPLE 232

550 g of the product obtained in Example 231 were slowly added at room temperature to 1,500 g of concentrated hydrochloric acid, and the mixture was then heated to 35°–40° C.

At that temperature, 255 g of chlorine were passed in, and the mixture was stirred at 35°–40° C. until the reaction had ended, which took about 12 hours.

After cooling to 10° C., the precipitated product was filtered off, washed with a little 20% strength NaCl solution and dried at 30° C. under reduced pressure.

647 g were obtained of a salt-containing product of the following constitution:

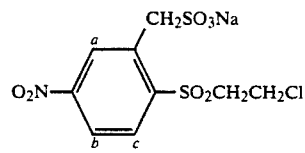

$^1$H-NMR: 3.82 (t, $CH_2$), 4.25 (t, $CH_2$), 4.55 (s, $CH_2$), 5.65 (s, $SO_3H$), 8.20 (d, aromatic -$H^c$), 8.30 (dd, aromatic -$H^b$), 8.60 (d, aromatic -$H^a$).

EXAMPLE 233

300 g of the nitro compound obtained in Example 232 were dissolved in 3,000 g of 1:1 (v/v) methanol/water and hydrogenated at room temperature with hydrogen in the presence of a palladium catalyst (10% strength on carbon).

The catalyst was filtered off and the filtrate was reduced to dryness. This left 152 g of a colorless compound conforming to the following structure:

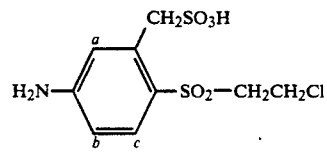

$^1$H-NMR: 3.65 (t, $CH_2$), 4.00 (t, $CH_2$), 4.20 (s, $CH_2$), 4.50 (br, s, $NH_2$), 6.60 (dd, aromatic -$H^b$), 6.90 (d, aromatic -$H^a$), 7.50 (d, aromatic -$H^c$).

The same method was used to obtain the anilines of the formula

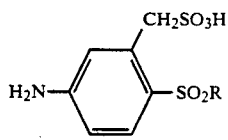

listed in Table 13.

TABLE 13

| Ex. No. | R |
|---|---|
| 238 | $CH=CH_2$ |
| 239 | $CH_2CH_2OH$ |
| 240 | $CH_2CH_2OSO_3H$ |
| 241 | $CH_2CH_2SSO_3H$ |

We claim:

1. A reactive dye of the formula I

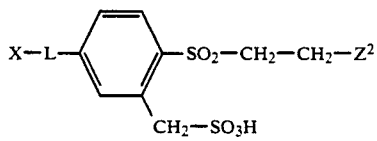

wherein
$Z^2$ is chlorine,
X is
 a) the radical of a chromophore which may contain a further reactive group and is derived from a metallized or unmetallized monoazo or disazo dye, from a triphendioxazine, from an anthraquinone, from a copper formazan or from a metallized phthalocyanine, or
 b) the radical of a coupling component to which may be additionally attached the radical of a diazo component via an azo linkage and which may contain an additional reactive group, and L is a bridge member of the formula

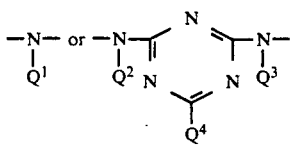

wherein $Q^1$ is hydrogen or $C_1-C_4$-alkyl, $Q^2$ and $Q^3$ are identical or different and each is independently of the other hydrogen or $C_1-C_4$-alkyl, and $Q^4$ is a leaving group.

2. The reactive dye of claim 1, wherein L is

3. The reactive dye of claim 1, wherein L is

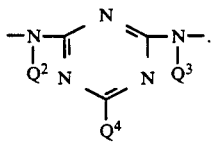

4. The reactive dye of claim 1, wherein X is the radical of a chromophore which may contain a further reactive group and is derived from a metallized or unmetallized monoazo or disazo dye, from a triphendioxazine, from an anthraquinone, from a copper formazan or from a metallized phthalocyanine.

5. The reactive dye of claim 1, wherein X is the radical of a coupling component to which may be additionally attached the radical of a diazo component via an azo linkage and which may contain an additional reactive group.

* * * * *